United States Patent
Hlavinka et al.

(10) Patent No.: US 10,544,080 B2
(45) Date of Patent: Jan. 28, 2020

(54) CONTINUOUS PROCESS FOR THE CONVERSION OF OLEFINS AND CARBON DIOXIDE TO ACRYLATES VIA SOLUTION PHASE REACTOR

(71) Applicant: CHEVRON PHILLIPS CHEMICAL COMPANY LP, The Woodlands, TX (US)

(72) Inventors: Mark L. Hlavinka, Tulsa, OK (US); Gregory G. Hendrickson, Kingwood, TX (US); Pasquale Iacono, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 16/001,171

(22) Filed: Jun. 6, 2018

(65) Prior Publication Data
US 2018/0362436 A1 Dec. 20, 2018

Related U.S. Application Data

(60) Provisional application No. 62/519,541, filed on Jun. 14, 2017.

(51) Int. Cl.
C07C 51/15 (2006.01)
C07C 51/14 (2006.01)
(Continued)

(52) U.S. Cl.
CPC ........... *C07C 51/15* (2013.01); *B01J 31/22* (2013.01); *B01J 31/2295* (2013.01); *C07C 51/41* (2013.01)

(58) Field of Classification Search
CPC .......... C07C 51/15; C07C 51/41; B01J 31/22; B01J 31/2295
See application file for complete search history.

(56) References Cited

U.S. PATENT DOCUMENTS 3,390,128 A 6/1968 Hughes et al.
3,623,973 A 11/1971 Tarhan
(Continued)

FOREIGN PATENT DOCUMENTS

CA 2791834 A1 9/2011
CN 103785469 A 5/2014
(Continued)

OTHER PUBLICATIONS

Al-Ghamdi, et al.., "Activity Relationship to Screen Ni-Bisphosphine Complexes for the Oxidative Coupling of CO2 and Ethylene," Organometallics, 2017, vol. 36, pp. 1107-1112.
(Continued)

*Primary Examiner* — Yate' K Cutliff
(74) *Attorney, Agent, or Firm* — Eversheds Sutherland (US) LLP

(57) ABSTRACT

Disclosed is a continuous process for producing α,β-unsaturated carboxylic acids or salts thereof, comprising: 1) in a first stage, contacting (a) a transition metal precursor compound comprising at least one first ligand, (b) optionally, at least one second ligand, (c) an olefin, (d) carbon dioxide ($CO_2$), and (e) a diluent to form a first composition; 2) in a second stage, contacting a polyanionic solid with the first composition to form a second composition; and 3) in a third stage, (a) contacting the second composition with a polar solvent to release a metal salt of an α,β-unsaturated carboxylic acid and form a reacted solid. Methods of regenerating the polyanionic solid are described.

25 Claims, 2 Drawing Sheets

(51) Int. Cl.
B01J 31/22 (2006.01)
C07C 51/41 (2006.01)

(56) References Cited

U.S. PATENT DOCUMENTS

| | | | |
|---|---|---|---|
| 4,060,480 A | 11/1977 | Reed et al. |
| 4,452,910 A | 6/1984 | Hopkins et al. |
| 4,792,620 A | 12/1988 | Paulik et al. |
| 5,376,611 A | 12/1994 | Shveima |
| 6,107,230 A | 8/2000 | McDaniel et al. |
| 6,165,929 A | 12/2000 | McDaniel et al. |
| 6,294,494 B1 | 9/2001 | McDaniel et al. |
| 6,300,271 B1 | 10/2001 | McDaniel et al. |
| 6,316,553 B1 | 11/2001 | McDaniel et al. |
| 6,355,594 B1 | 3/2002 | McDaniel et al. |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel et al. |
| 6,524,987 B1 | 2/2003 | Collins et al. |
| 6,548,441 B1 | 4/2003 | McDaniel et al. |
| 6,548,442 B1 | 4/2003 | McDaniel et al. |
| 6,576,583 B1 | 6/2003 | McDaniel et al. |
| 6,613,712 B1 | 9/2003 | McDaniel et al. |
| 6,632,894 B1 | 10/2003 | McDaniel et al. |
| 6,667,274 B1 | 12/2003 | Hawley et al. |
| 6,750,302 B1 | 6/2004 | McDaniel et al. |
| 6,831,141 B2 | 12/2004 | McDaniel et al. |
| 6,936,667 B2 | 8/2005 | Jensen et al. |
| 6,992,032 B2 | 1/2006 | McDaniel et al. |
| 7,026,494 B1 | 4/2006 | Yang et al. |
| 7,041,617 B2 | 5/2006 | Jensen et al. |
| 7,148,298 B2 | 12/2006 | Jensen et al. |
| 7,199,073 B2 | 4/2007 | Martin et al. |
| 7,226,886 B2 | 6/2007 | Jayaratne et al. |
| 7,250,510 B2 | 7/2007 | Organ et al. |
| 7,294,599 B2 | 11/2007 | Jensen et al. |
| 7,312,283 B2 | 12/2007 | Martin et al. |
| 7,470,758 B2 | 12/2008 | Jensen et al. |
| 7,501,372 B2 | 3/2009 | Thorn et al. |
| 7,517,939 B2 | 4/2009 | Yang et al. |
| 7,576,163 B2 | 8/2009 | Yang et al. |
| 7,601,665 B2 | 10/2009 | McDaniel et al. |
| 7,619,047 B2 | 11/2009 | Yang et al. |
| 7,629,284 B2 | 12/2009 | Jensen et al. |
| 7,884,163 B2 | 2/2011 | McDaniel et al. |
| 8,309,485 B2 | 11/2012 | Yang et al. |
| 8,592,632 B2 | 11/2013 | Dahmen et al. |
| 8,623,793 B2 | 1/2014 | McDaniel et al. |
| 8,623,973 B1 | 1/2014 | McDaniel et al. |
| 8,642,803 B2 | 2/2014 | Limbach et al. |
| 8,697,909 B2 | 4/2014 | Limbach et al. |
| 8,703,886 B1 | 4/2014 | Yang et al. |
| 8,940,940 B2 | 1/2015 | Dehn et al. |
| 9,023,959 B2 | 5/2015 | McDaniel et al. |
| 9,416,087 B2 | 8/2016 | Hlavinka et al. |
| 9,725,393 B2 | 8/2017 | Hlavinka et al. |
| 9,783,478 B2 | 10/2017 | Hlavinka et al. |
| 9,896,405 B2 | 2/2018 | Hlavinka et al. |
| 10,011,551 B2 | 7/2018 | Limbach et al. |
| 10,138,196 B2 | 11/2018 | Schaub et al. |
| 10,155,711 B2 | 12/2018 | Hlavinka et al. |
| 10,155,712 B2 | 12/2018 | Hlavinka et al. |
| 10,160,711 B2 | 12/2018 | Iacono et al. |
| 2010/0076167 A1 | 3/2010 | McDaniel et al. |
| 2011/0218359 A1 | 9/2011 | Limbach et al. |
| 2013/0172616 A1 | 7/2013 | Limbach et al. |
| 2015/0343431 A1 | 12/2015 | Parvulescu et al. |
| 2015/0344394 A1 | 12/2015 | Parvulescu et al. |
| 2016/0102039 A1 | 4/2016 | Hlavinka et al. |
| 2016/0130208 A1 | 5/2016 | Schaffner et al. |
| 2016/0229782 A1 | 8/2016 | Hlavinka et al. |
| 2016/0311745 A1 | 10/2016 | Hlavinka et al. |
| 2017/0166506 A1 | 6/2017 | Iacono et al. |
| 2017/0283356 A1 | 10/2017 | Hlavinka et al. |
| 2017/0349523 A1 | 12/2017 | Hlavinka et al. |
| 2018/0127346 A1 | 5/2018 | Hlavinka et al. |
| 2018/0362434 A1 | 12/2018 | Iacono et al. |
| 2018/0362435 A1 | 12/2018 | Iacono et al. |
| 2019/0062250 A1 | 2/2019 | Hlavinka et al. |
| 2019/0071381 A1 | 3/2019 | Iacono et al. |

FOREIGN PATENT DOCUMENTS

| | | |
|---|---|---|
| CN | 103785470 | 5/2014 |
| CN | 104418719 A | 3/2015 |
| CN | 104418736 A | 3/2015 |
| CN | 104418737 A | 3/2015 |
| CN | 105622383 A | 6/2016 |
| CN | 105622400 A | 6/2016 |
| DE | 112014001125 A5 | 11/2015 |
| EP | 2797869 | 8/2018 |
| EP | 3142992 | 9/2018 |
| IN | 201207472 P4 | 12/2013 |
| IN | 201404656 P4 | 9/2015 |
| WO | 2011/107559 A2 | 9/2011 |
| WO | 2011/107559 A3 | 12/2011 |
| WO | 2013/098772 A1 | 7/2013 |
| WO | 2013/186238 A1 | 12/2013 |
| WO | 2014/003195 A1 | 1/2014 |
| WO | 2014/130410 A1 | 8/2014 |
| WO | 2014/198469 A1 | 12/2014 |
| WO | 2015/018793 A1 | 2/2015 |
| WO | 2015/132031 A1 | 9/2015 |
| WO | 2015/173276 A1 | 11/2015 |
| WO | 2015/173277 A1 | 11/2015 |
| WO | 2015/173295 A1 | 11/2015 |
| WO | 2015/173296 A1 | 11/2015 |
| WO | 2015/173307 A1 | 11/2015 |
| WO | 2015/197699 A1 | 12/2015 |
| WO | 2016/057449 A1 | 4/2016 |
| WO | 2017106176 | 6/2017 |
| WO | 2017/178282 A1 | 10/2017 |

OTHER PUBLICATIONS

Brand, et al., "Acid-Base Characterization of Aluminum Oxide Surfaces with XPS" J. Phys. Chem. B. 2004, 108, p. 6017-6024.
Bruckmeier et al., "Formation of Methyl Acrylate from CO2 and Ethylene via Methylation of Nickelalactones", Organometallics, 2010, vol. 29, pp. 2199-2202.
Deutschmann, "Heterogeneous Catalysis and Solid Catalysts, 2. Development and Types of Solid Catalysts," Ullmann's Encyclopedia of Industrial Chemistry, published online Oct. 15, 2011, pp. 483-549, doi: 10.1002/14356007. o05_o02.
Eigenberger, "Catalytic Fixed-Bed Reactors," Ullmann's Encyclopedia of Industrial Chemistry, 2012, pp. 1-66, doi:10.1002/14356007. b04_199.pub2.
Final Office Action for U.S. Appl. No. 15/091,794, dated Feb. 7, 2017.
Fischer, et al.., "A key step in the formation of acrylic acid from CO2 and ethylene: the transformation of a Nickelalactone into a nickel-acrylate complex"; Chem. Commun., 2006, pp. 2510-2512.
Fischer et al., "Zur Synthese und Charakterisierung van N, N'-Tetramethylethylendiamin-nickelacyclopropionat", Z. anorg. allg. Chem., 1989, vol. 577, pp. 111-114.
Gordillo et al. "Catalytic route to acrylates from alkenes and CO2" Abstracts of Papers, 245th ACS National Meeting & Exposition, New Orleans, LA, United States, Apr. 7-11, 2013 (2013), INOR-1109. Language: English, Database: CAPLUS.
Hendricksen, "Catalytic Formation of Acrylate from Carbon Dioxide and Ethene," Chemistry, a European Journal, 2014, vol. 20, pp. 12037-12040.
Hoberg et al., "Nickel(O)-Induzierte C-C-Verknüipfung Zwischen Kohlendioxid und Ethylen Sowie Mono-Oder Di-Substituierten Alkenen"; Journal of Organometallic Chemistry, 1983, vol. 251, pp. C51-C53.
Huguet et al., "Nickel-Catalyzed Direct Carboxylation of Olefins with CO2: One-Pot Synthesis of a, β-Unsaturated Carboxylic Acid Salts", Chem. Eur. J., 2014, vol. 20, pp. 16858-16862.

(56) References Cited

OTHER PUBLICATIONS

International Search Report and the Written Opinion of the International Searching Authority in PCT/US2017/025837 dated Jul. 17, 2017, 9 pages.
International Search Report and Written Opinion for PCT/US2016/066360, dated Jul. 27, 2017, 8 pages.
International Search Report and Written Opinion of the Kal Searching Authority, PCT/US2015/054128, dated Dec. 21, 2015, 11 pages.
Jin et al., "Effect of Sodium Cation on Metallacycle β-Hydride Elimination in CO2-Ethylene Coupling to Acrylates", Chem. Eur. J., 2014, vol. 20, pp. 1-8.
Jin et al., "Lewis Acid Induced β-Elimination from a Nickelalactone: Efforts toward Acrylate Production from CO2 and Ethylene", Organometallics, 2013, vol. 32, pp. 2152-2159.
Knopf et al., "A family of cis-macrocyclic diphosphines: modular, stereoselective synthesis and application in catalytic CO2/ethylene coupling", Chemical Science, 2017, vol. 8 (Issue 2), pp. 1463-1468. doi:10.1039/c6sc03614g.
Kraus, "Ni-Catalyzed Synthesis of Acrylic Acid Derivatives from CO2 and Ethylene," Topics in Organometallic Chemistry, vol. 53, 2015, p. 199-223.
Langer et al., "A new set of nickelacyclic carboxylates ("nickelalactones") containing pyridine as supporting ligand: synthesis, structures and application in C-C- and C-S linkage reactions"; Journal of Organometallic Chemistry, 2004, vol. 689, pp. 2952-2962.
Krillov et al., "Carboxylic acid derivatives via catalytic carboxylation of unsaturated hydrocarbons: whether the nature of a reductant may determine the mechanism of CO2 incorporation?", Dalton Trans., 2015, vol. 44, 16212-16223.
Lejkowski et al, "The First Catalytic Synthesis of an Acrylate from CO2 and an Alkene—A Rational Approach"; Chem. Eur. J., 2012, vol. 18, pp. 14017-14025.
Limbach, "Acrylates from Alkenes and CO2, the Stuff That Dreams Are Made of," Advances in Organometallic Chemistry 2015, vol. 63, Chapter 4, pp. 175-202.
Limbach, et al., "CO2 as C1 building block for the synthesis of acrylates and beyond", From Abstracts of Papers, 247th ACS National Meeting & Exposition, Dallas, TX, United States, Mar. 16-20, 2014 (2014), CATL-116. Language: English, Database: CAPLUS.
Limbach et al., "Investigation of fundamental steps in the formation of acrylates from CO2 and ethylene", Abstracts of Papers, 243rd ACS National Meeting & Exposition, San Diego, CA, United States, Mar. 25-29, 2012 (2012), NOR-1216. Language: English, Database: CAPLUS.

Manzini et al., "Enhanced activity and recyclability of palladium complexes in the catalytic synthesis of sodium acrylate from CO2 and ethylene" ChemCatChem, 2016. doi:10.1002/cctc.201601150.
Manzini et al., "Palladium- and Nickel-Catalyzed Synthesis of Sodium Acrylate from Ethylene, CO2, and Phenolate Bases: Optimization of the Catalytic System fora Potential Process", Eur. J. Org. Chem., 2015, pp. 7122-7130.
Manzini et al., "Synthesis of acrylates from olefins and CO2 using sodium alkoxides as bases", Catalysis Today, 2016, http://dx.doi.org/10.1016/tcattod.2016.03.025.
Newkirk, "Drying and Decomposition of Sodium Carbonate," Analytical Chemistry, vol. 30, No. 5, 1958, pp. 982-984.
Non-Final Office Action for U.S. Appl. No. 15/203,844, dated Jan. 12, 2017.
Non-Final Office Action for U.S. Appl. No. 14/509,082 dated Nov. 5, 2015.
Norskov et al., Nature Chemistry, Towards the Computational Design of Solid Catalysts, 2009, 1, pp. 37-46.
Papai et al., "Mechanistic Details of Nickel(O)-Assisted Oxidative Coupling of CO2 with C2H4"; Organometallics, vol. 23, pp. 5252-5259, 2004.
Pinnavaia, T. J., "Intercalated Clay Catalysts," Science, 1983, vol. 220, No. 4595, pp. 365-371.
Plessow et al., "Acrylate Formation from CO2 and Ethylene Mediated by Nickel Complexes: A Theoretical Study", Oganometallics, 2014, vol. 33, pp. 3657-3668.
Plessow et al., "Mechanistic Details of the Nickel-Mediated Formation of Acrylates from CO2, Ethylene and Methyllodide", Organometallics, 2013, vol. 32, pp. 3327-3338.
Prasetyo, "Development of heterogenized catalyst systems for the synthesis of acrylic acid derivatives from carbon dioxide and ethylene," University of Stuttgart, Doctoral Thesis, Date of oral test: Apr. 20, 2015, 275 pages.
Stieber et al., "Acrylate formation from CO2 and ethylene: catalysis with palladium and mechanistic insight", Chem. Commun., 2015, vol. 51, pp. 10907-10909.
Thomas, J.M., "Sheet Silicate Intercalates: New Agents for Unusual Chemical Conversions*", Intercalation Chemistry, Academic Press, Inc., 1982, Ch. 3, pp. 55-99.
Wang, "Synthesis of Acrylic Acid Derivatives from CO2 and Ethylene," Chem, 3, 211-228, 2017.
Yu et al., "Carboxylation of olefins/alkynes with CO2 to industrially relevant acrylic acid derivatives", Journal of CO2 Utilization, 2013, vol. 1, pp. 60-68.
Jin et al., "Effect of Sodium Cation on Metallacycle β-Hydride Elimination in CO2-Ethylene Coupling to Acrylates", Chem. Eur. J., 2014, vol. 20, pp. 3205-3211.
International Search Report and Written Opinion for PCT/US2018/036427, dated Sep. 6, 2018, 8 pages.

CONTINUOUS PROCESS FOR THE CONVERSION OF OLEFINS AND CARBON DIOXIDE TO ACRYLATES VIA SOLUTION PHASE REACTOR

CROSS REFERENCE TO RELATED APPLICATIONS

This application claims the benefit of priority of U.S. Provisional Patent Application No. 62/519,541, filed Jun. 14, 2017, which is incorporated herein by reference in its entirety.

TECHNICAL FIELD

This disclosure relates to routes of synthesis of acrylic acid and other α,β-unsaturated carboxylic acids, including catalytic methods.

BACKGROUND

The majority of industrially synthesized chemical compounds are prepared from a limited set of precursors, whose ultimate sources are primarily fossil fuels. As these reserves diminish, it would be beneficial to use a renewable resource, such as carbon dioxide, which is a non-toxic, abundant, and economical $C_1$ synthetic unit. The coupling of carbon dioxide with other unsaturated molecules holds tremendous promise for the direct preparation of molecules currently prepared by traditional methods not involving $CO_2$.

One could envision the direct preparation of acrylates and carboxylic acids through this method, when carbon dioxide is coupled with olefins. Currently, acrylic acid is produced by a two-stage oxidation of propylene. The production of acrylic acid directly from carbon dioxide and ethylene would represent a significant improvement due to the greater availability of ethylene and carbon dioxide versus propylene, the use of a renewable material ($CO_2$) in the synthesis, and the replacement of the two-step oxygenation process currently being practiced.

Therefore, what is needed are improved methods for preparing acrylic acid and other α,β-unsaturated carboxylic acids, including catalytic methods.

SUMMARY OF THE DISCLOSURE

This summary is provided to introduce various concepts in a simplified form that are further described below in the detailed description. This summary is not intended to identify required or essential features of the claimed subject matter nor is the summary intended to limit the scope of the claimed subject matter.

In an aspect, this disclosure provides processes, including catalytic processes, for producing α,β-unsaturated carboxylic acids or salts thereof utilizing a soluble or an insoluble polyanionic solid (anionic polyelectrolyte) system. In particular, disclosed herein is a continuous process for producing an α,β-unsaturated carboxylic acid or salt thereof. When the polyanionic solid system is insoluble or the reaction system is otherwise heterogeneous, these processes represent an improvement over homogeneous processes that result in poor yields and involve challenging separation/isolation procedures. Moreover, the insoluble polyanionic solid system is advantageous for the development of a continuous process. Therefore, conventional methods generally make isolation of the desired α,β-unsaturated carboxylic acid (e.g., acrylic acid) difficult. In contrast, the processes disclosed herein utilize an polyanionic solid comprising associated metal cations that generally provides a heterogeneous reaction mixture. When combined with a catalyst such as a nickel catalyst, ethylene and carbon dioxide can be coupled to form a metalalactone, and the polyanionic solid can subsequently destabilize the metalalactone which eliminates a metal acrylate. By developing the disclosed heterogeneous system, there is now provided a distinct advantage in ease of separation of the desired product from the catalytic system. Moreover, the polyanionic solid can result in surprisingly high yields of the desired α,β-unsaturated carboxylic acid, such as acrylic acid.

According to an aspect, one continuous process for producing an α,β-unsaturated carboxylic acid, or a salt thereof, can comprise:

1) in a first stage, contacting (a) a transition metal precursor compound comprising at least one first ligand, (b) optionally, at least one second ligand, (c) an olefin, (d) carbon dioxide ($CO_2$), and (e) a diluent to form a first composition; and
2) in a second stage, contacting a polyanionic solid with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid.

In a further aspect, there is provided another such continuous process for producing an α,β-unsaturated carboxylic acid or salt thereof, and this process can comprise:

1) in a first stage, contacting (a) a transition metal precursor compound comprising at least one first ligand, (b) optionally, at least one second ligand, (c) an olefin, (d) carbon dioxide ($CO_2$), and (e) a diluent to form a first composition comprising a metalalactone compound; and
2) in a second stage, contacting a polyanionic solid with the first composition to form a second composition; and
3) in a third stage, (a) contacting the second composition with polar solvent to release a metal salt of an α,β-unsaturated carboxylic acid and form a reacted solid; and (b) contacting the reacted solid with a metal-containing base to produce a regenerated polyanionic solid.

In this aspect, for example, the first composition includes a metalalactone compound that is formed from the recited reactants and, in addition to the metalalactone portion of the molecule, the metalalactone compound can include at least one additional ligand, which can be at least one first ligand and/or at least one second ligand. For example, a transition metal precursor compound can be $Ni(COD)_2$, and one suitable second ligand can be a diphosphine ligand, and the metalalactone compound can comprise the nickelalactone moiety and the diphosphine ligand.

According to this and other aspects of the disclosure, the metalalactone compound may also be described as a metalalactone comprising at least one ligand or simply a metalalactone, and these terms are used interchangeably to reflect that the metalalactone compound comprises at least one ligand in addition to the metalalactone moiety. Similarly, reference to a metalalactone ligand refers to any ligand of the metalalactone compound other than the metalalactone moiety.

The polyanionic solid and any associated cations such as associated metal cations are described in detail herein.

According to additional aspects of this disclosure, there is provided a continuous process for producing an α,β-unsaturated carboxylic acid or salt thereof, in which the process can comprise:
1) in a first stage, obtaining or providing a first composition comprising a metalalactone compound and a diluent;
2) in a second stage, contacting a polyanionic solid with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid.

In an aspect, in the second stage of this continuous process for producing an α,β-unsaturated carboxylic acid or salt thereof, the second composition can comprise an adduct of the metalalactone and the polyanionic solid.

In a further aspect, there is provided a continuous process for producing an α,β-unsaturated carboxylic acid or salt thereof, the process comprising:
1) in a first stage, contacting (a) a Group 8-10 transition metal precursor compound comprising at least one first ligand, (b) optionally, at least one second ligand, (c) an olefin, (d) carbon dioxide ($CO_2$), and (e) a diluent to form a first composition comprising a metalalactone compound; and
2) in a second stage, contacting an anionic polyaromatic resin comprising associated metal cations with the first composition to form a second composition comprising an adduct of the metalalactone compound and the anionic polyaromatic resin; and
3) in a third stage, (a) contacting the second composition with water to release a metal salt of an α,β-unsaturated carboxylic acid and form a reacted polyaromatic resin; and (b) contacting the reacted polyaromatic resin with a metal-containing base to produce a regenerated polyanionic solid.

This summary and the following detailed description provide examples and are explanatory only of the invention. Accordingly, the foregoing summary and the following detailed description should not be considered to be restrictive. Additional features or variations thereof can be provided in addition to those set forth herein, such as for example, various feature combinations and sub-combinations of these described in the detailed description.

BRIEF DESCRIPTION OF THE DRAWINGS

FIG. 2 illustrates 1) a first stage in which a nickel precursor compound comprising at least one first ligand (Ln-Ni), optionally, at least one second ligand (also generically represented as Ln), ethylene, carbon dioxide ($CO_2$), and toluene (a diluent) are combined to form a first composition which includes a nickelalactone; 2) a second absorption/ elimination stage, in which a polyanionic solid (also termed cocatalyst or activator) is contacted with the first composition to form a second composition, which can include an adduct of the nickelalactone and the polyanionic solid; and 3) a third stage in which (a) the second composition (typically comprising the nickelalactone-polyanionic solid adduct) is contacted with a polar solvent to release a metal salt of an α,β-unsaturated carboxylic acid and form a reacted solid, and (b) reacted solid (cocatalyst) is contacted with a metal-containing base to produce a regenerated polyanionic solid. FIG. 2 also illustrates an optional fourth stage in which the regenerated polyanionic solid is dried or partially dried. The dashed lines between the second stage, third stage and optional fourth stage are to illustrate that the vessels alternate between the stages.

DETAILED DESCRIPTION OF THE DISCLOSURE

Definitions

Figure 1:
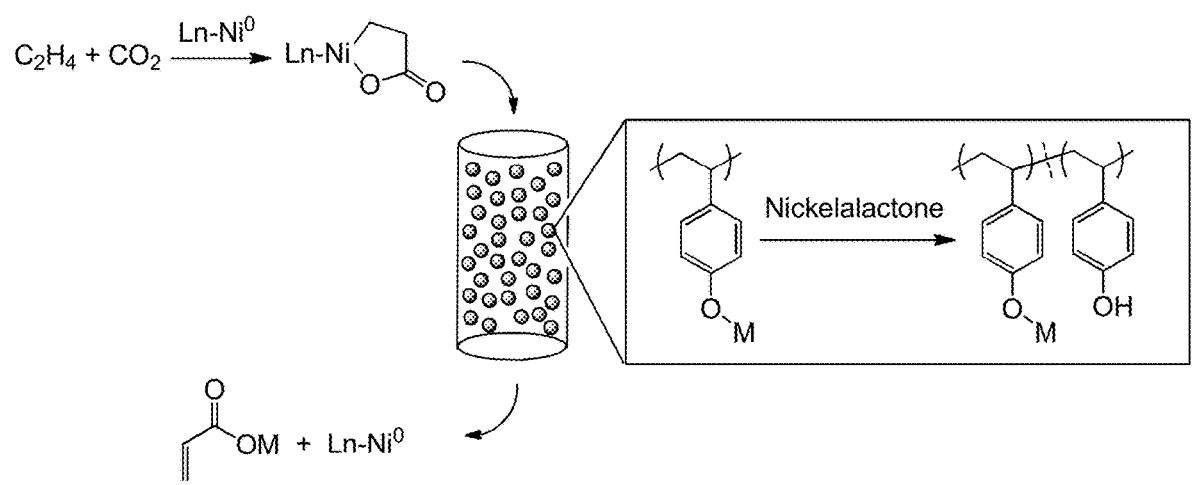
FIG. 1. illustrates an aspect of this disclosure, showing the use an polyanionic solid stationary phase in a column configuration, in which formation of the acrylate coupling reaction of ethylene and $CO_2$ to form a metalalactone such as a nickelalactone in a mobile phase can be effected, and the resulting nickelalactone destabilized by the polyelectrolyte stationary phase to form an acrylate product.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While compositions and methods are described in terms of "comprising" various components or steps, the compositions and methods can also "consist essentially of" or "consist of" the various components or steps, unless stated otherwise.

The terms "a," "an," and "the" are intended to include plural alternatives, e.g., at least one. For instance, the disclosure of "a polyanionic solid," "a diluent," "a catalyst," and the like, is meant to encompass one, or mixtures or combinations of more than one, polyanionic solid, diluent, catalyst, and the like, unless otherwise specified.

The terms "including", "with", and "having", as used herein, are defined as comprising (i.e., open language), unless specified otherwise.

The term "hydrocarbon" refers to a compound containing only carbon and hydrogen. Other identifiers can be utilized to indicate the presence of particular groups in the hydrocarbon, for instance, a halogenated hydrocarbon indicates the presence of one or more halogen atoms replacing an equivalent number of hydrogen atoms in the hydrocarbon.

As used herein, the term "α,β-unsaturated carboxylic acid" and its derivatives refer to a carboxylic acid having a carbon atom of a carbon-carbon double bond attached to the carbonyl carbon atom (the carbon atom bearing the double bonded oxygen atom). Optionally, the α,β-unsaturated carboxylic acid can contain other functional groups, heteroatoms, or combinations thereof.

The term "polyanionic" is used interchangeably with "anionic polyelectrolyte" and is used to mean a polymeric (macromolecular), organic or inorganic, extended substance which comprises a multiply-charged polyion, together with an equivalent amount of counter ions. Therefore, a "polyanionic solid" or "anionic polyelectrolyte" refers to a material that comprises a multiply-charged polyanion, together with an equivalent amount of cations. The charge on the polyion typically resides on heteroatoms such as oxygen, nitrogen or sulfur, or on groups such as sulfonate. The structural part of the polyelectrolyte that bears the charged moieties can be pendant groups off a polymer backbone or can be part of the polymeric backbone itself. The term "polyelectrolyte" or "polyanionic" material may be used to refer to both soluble species and insoluble species, such as some of the poly(vinylphenol)-based materials, the phenol-formaldehyde based materials described herein, or the chemically-treated solid oxide materials described herein. The multiply-charged polyanion may also be referred to as a base, and the associated metal ion as simply a counter ion, metal ion, or Lewis acid as appropriate.

Although the terms "polyphenol" and "polyaromatic" are used herein to describe polyanionic materials in which a phenoxide moiety carries the negative charge in the polyelectrolyte, and although these terms may be used interchangeably as the context allows, these terms are generally used herein to describe specific types of polyanionic materials or anionic polyelectrolyte polymers, that are somewhat different, as set out here.

[1] The terms "polyphenol" and "polyphenoxide" are generally used herein to describe a specific type of anionic polyelectrolyte polymer, for example, the polymeric materials such as poly(4-vinylphenol) and metallated poly(4-vinylphenoxide) that typically include a pendant phenol, phenoxide, or substituted analogs thereof that are bonded to a polymeric backbone. Therefore, the oxygen of the phenoxide group bears the negative charge.

[2] The term "polyaromatic" is also generally used herein to describe a specific type of anionic polyelectrolyte resin or polymer, for example, the phenol-formaldehyde crosslinked resins and their analogs, in which the phenol aromatic group and methylene moieties are part of an extended crosslinked network. Therefore, aromatic groups in the "polyaromatic" structure are hydroxylated, hydroxymetallated, or otherwise functionalized with a group that carries the negative charge in the anionic polyelectrolyte (e.g. thiolate, alkyl amide). Crosslinked networks that are prepared using various phenol or polyhydroxyarene co-monomers also included in this definition. The term "phenolic resin" may be used to describe these materials as well.

A "polyhydroxyarene" is used herein to a phenol-type monomer that includes more than one hydroxyl group. Resorcinol (also termed, benzenediol or m-dihydroxybenzene) is a typical polyhydroxyarene.

The terms "chemically-treated solid oxide," "treated solid oxide," and the like, are used herein to indicate a solid, inorganic oxide of relatively high porosity, which can exhibit Lewis acidic or Brønsted acidic behavior, and which has been treated with an electron-withdrawing component, typically an anion, and generally which has been calcined. The electron-withdrawing component is typically an electron-withdrawing anion source compound. Thus, the chemically-treated solid oxide can comprise a calcined contact product of at least one solid oxide with at least one electron-withdrawing anion source compound. Typically, the chemically-treated solid oxide comprises at least one acidic solid oxide compound. The terms "activator", "activator-support", and "co-catalyst" are also used herein to describe the solid oxide chemically-treated with an electron withdrawing anion, or "chemically-treated solid oxide", and these terms may be used interchangeably, regardless of any actual activating mechanism.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Various numerical ranges are disclosed herein. When Applicants disclose or claim a range of any type, Applicants' intent is to disclose or claim individually each possible number that such a range could reasonably encompass, including end points of the range as well as any sub-ranges and combinations of sub-ranges encompassed therein, unless otherwise specified. For example, by disclosing a temperature of from 70° C. to 80° C., Applicant's intent is to recite individually 70° C., 71° C., 72° C., 73° C., 74° C., 75° C., 76° C., 77° C., 78° C., 79° C., and 80° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicants disclose in an aspect of the disclosure that one or more steps in the processes disclosed herein can be conducted at a temperature in a range from 10° C. to 75° C., this range should be interpreted as encompassing temperatures in a range from "about" 10° C. to "about" 75° C.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means±20% of the stated value, ±15% of the stated value, ±10% of the stated value, ±5% of the stated value, or ±3% of the stated value.

Applicants reserve the right to proviso out or exclude any individual members of any such group of values or ranges, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants can be unaware of at the time of the filing of the application.

The term "substituted" when used to describe a group, for example, when referring to a substituted analog of a particular group, is intended to describe the compound or group wherein any non-hydrogen moiety formally replaces hydrogen in that group or compound, and is intended to be non-limiting. A compound or group can also be referred to herein as "unsubstituted" or by equivalent terms such as "non-substituted," which refers to the original group or compound. "Substituted" is intended to be non-limiting and include inorganic substituents or organic substituents as specified and as understood by one of ordinary skill in the art.

The terms "contact product," "contacting," and the like, are used herein to describe compositions and methods wherein the components are contacted together in any order, in any manner, and for any length of time, unless specified otherwise. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

The present disclosure is directed generally to methods for forming α,β-unsaturated carboxylic acids, or salts thereof. An illustrative example of a suitable α,β-unsaturated carboxylic acid is acrylic acid.

Formation of α,β-unsaturated Carboxylic Acids and Salts

According to one aspect, this disclosure provides for the formation of an α,β-unsaturated carboxylic acids and salts thereof from metalalactones and polyanionic solids. One example of the α,β-unsaturated carboxylic acid salt formation from exemplary metalalactones and polyanionic solids is illustrated in Scheme 1, which provides for a nickel catalytic coupling reaction between an olefin and $CO_2$ and formation of an acrylate. As explained herein, Scheme 1 is not limiting but is exemplary, and each reactant, catalyst, polymer, and product are provided for illustrative purposes.

Scheme 1

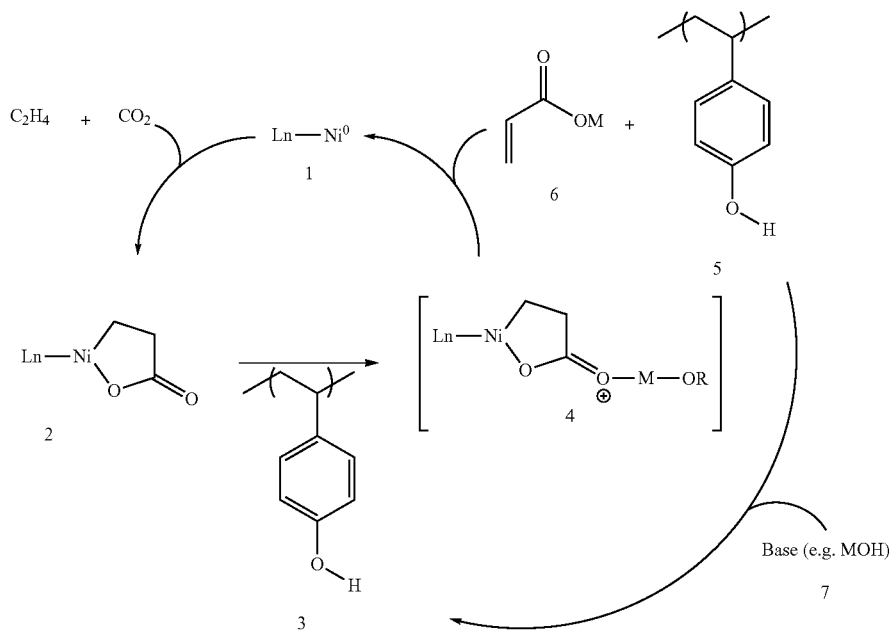

In Scheme 1, a transition metal catalyst as disclosed herein is illustrated generally by a nickel(0) catalyst at compound 1, and the olefin disclosed herein, generally an α-olefin, is illustrated generally by ethylene. In the presence of the catalyst 1, the olefin couples with $CO_2$ to form the metalalactone 2. Metalalactone 2 is destabilized by its interaction with an polyanionic solid, an example of which is shown in Scheme 1 as a metal poly(4-vinylphenoxide) 3. While not intending to be bound by theory, metal poly(4-vinylphenoxide) 3 is thought to interact with metalalactone 2 in some way, for example to form an adduct of some type, such as one illustrated as intermediate 4. Reaction with the combined metal poly(4-vinylphenoxide) 3 and metalalactone 2 (or intermediate of some type, represented generally as 4) then proceeds to eliminate or release the metal acrylate 6, for example, from intermediate 4, and regenerates catalyst compound 1 and byproduct neutral polymer 5 (here, poly(4-vinylphenol), which is regenerated to the polyanionic solid reactant, for example metal poly(4-vinylphenoxide) 3, upon its reaction with the base 7. The participation of the polar solvent and/or base in the elimination or release of the metal acrylate 6, is not fully understood at this time and may include direct participation in the mechanism or simply solvating an acrylate salt which is insoluble in the diluent. In other words, elimination of the metal acrylate from 4 occurs to regenerate catalyst compound 1 and byproduct neutral polymer 5 (here, poly(4-vinylphenol)), which is regenerated to the polyanionic solid reactant 3 upon its reaction with a base 7. In the presence of additional ethylene and $CO_2$, catalyst 1 is converted to metalalactone 2.

One exemplary base illustrated in Scheme 1 is a hydroxide base, but a carbonate base, similar inorganic bases, and a wide range of other bases can be used, particularly metal-containing bases. Metal containing bases can include any basic inorganic metal compound or mixture of compounds that contain metal cations or cation sources, for example, alkali and alkaline earth metal compounds such as oxides, hydroxides, alkoxides, aryloxides, amides, alkyl amides, arylamides, hydrides and carbonates like calcium carbonate. In an aspect, the reaction of Scheme 1 can be conducted using certain bases as disclosed, but if desired, other organic bases such as some alkoxide, aryloxide, amide, alkyl amide, arylamide bases, or the like can be excluded. Typically, the inorganic bases such as alkali metal hydroxides have been found to work well.

Polyanionic Solids (Anionic Polyelectrolytes) and Associated Cations

Generally, the polyanionic solid comprising associated metal cations used in the processes disclosed herein can comprise (or consist essentially of, or consist of) an insoluble polyanionic solid, a soluble anionic polyelectrolyte, or a combination thereof. That is, the polyanionic solid material can be soluble, insoluble, or only partially or slightly soluble in the diluent or reaction mixture. It is further contemplated that mixtures or combinations of two or more polyanionic solids can be employed in certain aspects of the disclosure. Therefore, the "polyanionic solid" is a polymeric or extended lattice solid, organic or inorganic material, which comprises a multiply-charged polyanion, together with an equivalent amount of counter cations, and is used generally to refer to both soluble materials and insoluble materials.

In an aspect, the polyanionic solid comprising associated cations can be used in the absence of an alkoxide or aryloxide base. Further, the reactions and processes disclosed herein can be conducted in the absence of an alkoxide, an aryloxide, an alkylamide, an arylamide, and/or substituted analogs thereof. That is, additional bases with their associated counter ions are not required to effect the processes disclosed herein.

According to an aspect, the polyanionic solid comprising associated cations used in the processes can be used in the absence of a solid support. That is the polyanionic solid can be used is its natural polymeric form without being bonded to or supported on any insoluble support, such as an inorganic oxide or mixed oxide material.

Alkoxylated Polymers and Related Polyanionic Solids

In an aspect, the term polyanionic solid (or anionic polyelectrolyte) is used to refer to and include such polyanionic solids that comprise alkoxide, aryloxide, acrylate, (meth)acrylate, sulfonate, alkyl thiolate, aryl thiolate, alkyl amide, or aryl amine groups, along with associated metal cations, such as any alkali metal cation, alkaline earth cation, or metal cations having varying Lewis acidities. While aspects of this disclosure are exemplified with polyanionic solids having aryloxide (or "phenoxide") anionic groups, these are to be considered exemplary of any of the polyanionic solids provided herein. Therefore, terms such as poly (vinyl aryloxide), poly(vinyl phenoxide), poly(hydroxystyrene), and the like are generally used interchangeably unless the context provides otherwise.

Accordingly, the term anionic polyelectrolyte or polyanionic solid is used generally to include such polyanionic solids as a poly(vinyl aryloxide), a poly(vinyl alkoxide), a poly(acrylate), a poly((meth)acrylate)), a poly(styrene sulfonate), a phenol-formaldehyde resin, a polyhydroxyarene-formaldehyde resin (such as a resorcinol-formaldehyde resin), a polyhydroxyarene- and fluorophenol-formaldehyde resin (such as a resorcinol- and 2-fluorophenol-formaldehyde resin), a poly(vinylarylamide), a poly(vinyl alkylamide), or combinations thereof, along with associated metal cations. Polymers that generally fall under the phenol-formaldehyde type of crosslinked resins may be referred to as polyaromatic resins. Co-polymers of these specific types of polyanionic solids are also included in this disclosure. The polyelectrolyte core structure can be substituted on the polymer backbone or the pendant groups that also contain the typical oxygen, nitrogen, or sulfur heteroatoms, and such substituted variations are included in this disclosure and use of the term polyanionic solid. For example, any of the polyanionic solids can be substituted with electron-withdrawing groups or electron-donating groups or even combinations thereof.

Anionic polyelectrolytes (polyanionic solids) such as those used herein include associated cations, particularly associated metal cations, including Lewis acidic metal cations and cations with low Lewis acidity. According to an aspect, the associated metal cations can be an alkali metal, an alkaline earth metal, or any combination thereof. Typical associated metal cations can be, can comprise, or can be selected from lithium, sodium, potassium, magnesium, calcium, strontium, barium, aluminum, or zinc, and the like. Generally, sodium or potassium associated metal cations have been found to work well. Therefore, cations with a range of Lewis acidities in the particular solvent can be useful according to this disclosure.

One aspect of the disclosed process provides for using an polyanionic solid that comprises, consists essentially of, or consists of sodium(polyvinylphenoxide), including sodium (poly-4-vinylphenoxide). Other salts, such as the potassium salt, of the poly-4-vinylphenoxide are also useful.

In a further aspect, useful polyanionic solids can include phenol-formaldehyde resins, which are cross-linked materials derived from the condensation reaction of phenol with formaldehyde, that are treated with a base or a metal cation source. Advantages of using treated phenol-formaldehyde resins include their insolubility, which allows the use of a range of solvents with these materials, and their relatively high phenol concentration that can be functionalized using a metal base such as an alkali metal hydroxide. An early version of the thermosetting phenol formaldehyde resins formed from the condensation reaction of phenol with formaldehyde is Bakelite®, and various phenol-formaldehyde resins used herein may be referred to generically as "Bakelite" resins. In the context of this disclosure, the use of terms such as Bakelite or general terms such as phenol-formaldehyde resins contemplates that these materials will be treated with a metal-containing base or a metal cation source such as sodium hydroxide prior to their use in the processes disclosed.

In addition, other useful polyanionic solids include substituted phenol-formaldehyde resins that are also generally crosslinked into insoluble resins. These resins can be formed from the condensation reaction of one or more of phenol, a polyhydroxyarene such as resorcinol (also, benzenediol or m-dihydroxybenzene), and/or their substituted analogs with formaldehyde. Therefore, these materials include resins made with more than one phenol as co-monomer. Treatment with bases such as NaOH or KOH also provides a ready method of functionalizing the polyaromatic polymers for the reactivity described herein.

In one example, a resin can be prepared using the monomer combination of resorcinol (m-dihydroxybenzene) and fluorophenol monomers with formaldehyde, and sodium-treated to generate the polyanionic solid. While not intending to be theory bound, the meta-dihydroxybenzene is believed to add additional ion chelation functionality to the resin. Subsequent base (e.g. sodium hydroxide) treatment can be used to generate the polyanionic solid.

Finally, this aspect is not intended to be limiting. Therefore, other suitable polyanionic solids that can be used include a number of polyanionic solids which include carboxylic acid/carboxylate groups. Examples include but are not limited to polyacrylic acid, polymethacrylic acid, poly(D,L-glutamic) acid, polyuronic acid (alginic, galacturonic, glucuronic, and the like), glycosaminoglycans (hyaluronic acid dermatan sulphate, chondroitin sulphate, heparin, heparan sulphate, and keratan sulphate), poly(D,L-aspartic acid), poly(styrene sulfonate), poly(phosphate), polynucleic acids, and so forth.

In those aspects and embodiments in which polymer support variations are used and/or in which the polyelectrolyte itself is a solid that is insoluble in the diluent of the reaction, such solid state polyelectrolyte embodiments can have any suitable surface area, pore volume, and particle size, as would be recognized by those of skill in the art. For instance, the solid polyelectrolyte can have a pore volume in a range from 0.1 to 2.5 mL/g, or alternatively, from 0.5 to 2.5 mL/g. In a further aspect, the solid polyelectrolyte can have a pore volume from 1 to 2.5 mL/g. Alternatively the pore volume can be from 0.1 to 1.0 mL/g. Additionally, or alternatively, the solid polyelectrolyte can have a BET surface area in a range from 10 to 750 m$^2$/g; alternatively, from 100 to 750 m$^2$/g; or alternatively, from 100 to 500 m$^2$/g or alternatively from 30 to 200 m$^2$/g. In a further aspect, the solid polyelectrolyte can have a surface area of from 100 to 400 m$^2$/g, from 200 to 450 m$^2$/g, or from 150 to 350 m$^2$/g. Surface area, pore diameter, and pore volume were measured by Brunauer, Emmett and Teller (BET) technique with nitrogen gas used as the probe. The average particle size of the solid polyelectrolyte can vary greatly depending upon the process specifics, however, average particle sizes in the range of from 5 to 500 µm, from 10 to 250 µm, or from 25 to 200 µm, are often employed. Alternatively ⅛ inch (3.2 mm) to ¼ inch (6.4 mm) pellets or beads can also be used. In an aspect, the average or median particle size is measured by either dynamic light scattering tests or by a laser diffraction technique.

The present disclosure also provides for various modifications of the polymeric anionic stationary phase (polyanionic solids), for example, in a column or other suitable solid state configuration. Further various modifications of the polymeric anionic stationary phase (polyanionic solids), for example, in a column or other suitable solid state configuration are useful in the processes disclosed herein. For example, acid-base reactions that generate the polyanionic solid from the neutral polymer can be effected using a wide range of metal bases, including alkali and alkaline hydroxides, alkoxides, aryloxides, amides, alkyl or aryl amides, and the like, such that an assortment of electrophiles can be used in nickelalactone destabilization as demonstrated herein for the polyvinylphenols.

Polymer modifications can also include using variants of the poly(vinylphenol), that can be prepared by polymerization of protected hydroxyl-substituted styrenes (such as acetoxystyrene) having a variety of organic and inorganic substituents, such as alkyls, halogens, and heteroatom substituents, typically followed by hydrolysis. Such adjustments can provide flexibility for tailoring the reaction according to the specific olefin to be coupled with $CO_2$, the reaction rate, the catalytic turnover, as well as additional reaction parameters and combinations of reaction parameters.

In a further aspect, polymer modifications can also include using co-polymers based on, for example, the co-polymerization of a protected hydroxyl-substituted styrene with other monomers (e.g., styrenes and/or (meth)acrylates) to produce libraries of polymeric electrophiles. Such a library can be utilized to test and match the specific polyanionic solid with the specific olefin, to improve or optimize reaction rate, catalytic turnover, reaction selectivity, and the like. Further polymer support variations can also be used, for example, polymers can be supported onto beads or other surfaces. Alternatively, one class of polymer support variation that is possible for use with this technology is the cast polymer that can function as an ion exchange membrane. Alternatively, the polyanionic solid can be unsupported and used in the absence of any support.

Chemically-Treated Solid Oxide as Polyanionic Solids

In one aspect, this disclosure encompasses a continuous process as described herein, in which the polyanionic solid (also termed an activator or co-catalyst) can comprise a metal oxide. In an aspect, the polyanionic solid can comprise a calcined metal oxide. Examples of metal oxides include, but are not limited to, silica, alumina, silica-alumina, silica-coated alumina, aluminum phosphate, aluminophosphate, heteropolytungstate, mullite, boehmite, titania, zirconia, magnesia, boria, zinc oxide, silica-titania, silica-zirconia, a mixed oxide thereof, or any mixture thereof. The polyanionic solid can comprise, for example, metal-treated sodium oxide. The polyanionic solid can comprise a solid oxide that has been contacted with the metal-containing base, for example, the polyanionic solid can comprise a chemically-treated solid oxide that has been hydroxylated and subsequently contacted with the metal-containing base.

In an aspect, the polyanionic solid can comprise, consist of, consist essentially or, or be selected from a chemically-treated solid oxide. The term "chemically-treated solid oxide" is used interchangeably with similar terms such as, "solid oxide treated with an electron-withdrawing anion," "treated solid oxide," While not intending to be bound by theory, it is thought that the chemically-treated solid oxide can serve as an acidic activator-support which allows it to function as the polyanionic solid in the continuous process disclosed herein.

In one aspect of this disclosure, the polyanionic solid can comprise at least one chemically-treated solid oxide comprising at least one solid oxide treated with at least one electron-withdrawing anion, wherein the solid oxide can comprise any oxide that is characterized by a high surface area, and the electron-withdrawing anion can comprise any anion that increases the acidity of the solid oxide as compared to the solid oxide that is not treated with at least one electron-withdrawing anion.

In another aspect of this disclosure, the polyanionic solid can comprise at least one chemically-treated solid oxide, comprising at least one solid oxide treated with at least one electron-withdrawing anion. For example, the solid oxide can comprise or can be selected from at least one of silica, alumina, silica-alumina, silica-coated alumina, aluminum phosphate, aluminophosphate, heteropolytungstate, mullite, boehmite, titania, zirconia, magnesia, boria, zinc oxide, silica-titania, silica-zirconia, a mixed oxide thereof, or any mixture thereof. These oxides can be chemically treated with at least one electron withdrawing anion to provide the polyanionic solid. For example, the at least one electron withdrawing anion can comprise or can be selected from fluoride, chloride, bromide, iodide, phosphate, triflate, trifluoroacetate, sulfate, bisulfate, fluorosulfate, fluoroborate, fluorophosphate, fluorozirconate, fluorotitanate, phosphotungstate, or similar anions, or any combination thereof.

In an aspect, the continuous process according to this disclosure, the chemically-treated solid oxide comprises, consists of, consists essentially of, or is selected from fluorided alumina, chlorided alumina, bromided alumina, fluorided-chlorided alumina, sulfated alumina, fluorided silica-alumina, chlorided silica-alumina, bromided silica-alumina, fluorided-chlorided silica-alumina, sulfated silica-alumina, fluorided silica-titania, chlorided silica-titania, bromided silica-titania, fluorided-chlorided silica-titania, sulfated silica-titania, fluorided silica-zirconia, chlorided silica-zirconia, bromided silica-zirconia, fluorided-chlorided silica-zirconia, sulfated silica-zirconia, fluorided silica-coated alumina, chlorided silica-coated alumina, bromided silica-coated alumina, fluorided-chlorided silica-coated alumina, sulfated silica-coated alumina, fluorided mullite, chlorided mullite, bromided mullite, fluorided-chlorided mullite, or sulfated mullite.

In another aspect and in any embodiment of this disclosure, for example, the chemically-treated solid oxide can comprise at least one silica-coated alumina treated with at least one electron-withdrawing anion, wherein: the at least one silica-coated alumina has a weight ratio of alumina to silica in a range from about 1:1 to about 100:1, and the at least one electron-withdrawing anion comprises fluoride, chloride, bromide, phosphate, triflate, bisulfate, sulfate, or any combination thereof.

In a further aspect, the chemically-treated solid oxide comprises, consists of, consists essentially of silica-coated alumina that has been fluorided and chlorided. In this aspect, the silica-coated alumina can comprise from about 10 to about 80 wt. % silica, based on the weight of the silica-coated alumina; the fluorided-chlorided silica-coated alumina comprises from about 2 to about 15 wt. % F, based on the weight of the fluorided-chlorided silica-coated alumina; and/or the fluorided-chlorided silica-coated alumina comprises from about 1 to about 10 wt. % Cl, based on the weight of the fluorided-chlorided silica-coated alumina. In this continuous process, the fluorided-chlorided silica-coated alumina can be produced by a process comprising: (a) calcining a silica-coated alumina at a peak calcining temperature to produce a calcined silica-coated alumina; (b) contacting the calcined silica-coated alumina with a chlorine-containing compound and calcining at a peak chloriding temperature to produce a chlorided silica-coated alumina; and (c) contacting the chlorided silica-coated alumina with a fluorine-containing compound and calcining at a peak fluoriding temperature to produce the fluorided-chlorided silica-coated alumina. The fluorided-chlorided silica-coated alumina can have, for example, a pore volume in a range from about 0.9 to about 2.0 mL/g; and a surface area in a range from about 200 to about 700 $m^2/g$.

In yet a further aspect and in any embodiment of this disclosure, the chemically-treated solid oxide can comprise the contact product of at least one solid oxide compound and at least one electron-withdrawing anion source. The solid oxide compound and electron-withdrawing anion source are described independently herein and may be utilized in any combination to further describe the chemically-treated solid oxide comprising the contact product of at least one solid oxide compound and at least one electron-withdrawing anion source. That is, the chemically-treated solid oxide is provided upon contacting or treating the solid oxide with the electron-withdrawing anion source. In an aspect, the solid oxide compound can comprise or can be selected from an inorganic oxide.

In an aspect, the solid oxide compound can be calcined prior to contacting with the electron-withdrawing anion source, though this is not required. In another aspect, the solid oxide compound can be calcined during or after contacting with the electron-withdrawing anion source. Thus, contact product of the solid oxide and the electron-withdrawing anion may be calcined either during or after the solid oxide compound is contacted with the electron-withdrawing anion source. In this aspect, the solid oxide compound may be calcined or uncalcined. In another aspect, the polyanionic solid may comprise the contact product of at least one calcined solid oxide compound and at least one electron-withdrawing anion source.

While not intending to be bound by theory, the chemically-treated solid oxide is thought to function as a co-catalyst or activator when used as disclosed herein. Moreover, the chemically-treated solid oxide is thought to function as a better co-catalyst or activator as compared to the non-chemically-treated oxide. The activation function of the chemically-treated solid oxide is evident in the enhanced activity of polyanionic solid as a whole, as compared to a polyanionic solid containing the corresponding untreated solid oxide.

In one aspect, the chemically-treated solid oxide of this disclosure can comprise a solid inorganic oxide material, a mixed oxide material, or a combination of inorganic oxide materials, that is chemically-treated with an electron-withdrawing component, and optionally treated with a metal. Thus, the solid oxide of this disclosure encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound, and are encompassed by this disclosure. The solid inorganic oxide material, mixed oxide material, combination of inorganic oxide materials, electron-withdrawing component, and optional metal are independently described herein and may be utilized in any combination to further described the chemically-treated solid oxide.

In one aspect of this disclosure, the chemically-treated solid oxide further can comprise a metal or metal ion selected from zinc, nickel, vanadium, titanium, silver, copper, gallium, tin, tungsten, molybdenum, or any combination thereof; alternatively, the chemically-treated solid oxide further can comprise a metal or metal ion selected from zinc, nickel, vanadium, titanium, or tin, or any combination thereof; alternatively, the chemically-treated solid oxide can further comprise a metal or metal ion selected from zinc, nickel, vanadium, tin, or any combination thereof.

Examples of chemically-treated solid oxides that further comprise a metal or metal ion include, but are not limited to, zinc-impregnated chlorided alumina, titanium-impregnated fluorided alumina, zinc-impregnated fluorided alumina, zinc-impregnated chlorided silica-alumina, zinc-impregnated fluorided silica-alumina, zinc-impregnated sulfated alumina, chlorided zinc aluminate, fluorided zinc aluminate, sulfated zinc aluminate, or any combination thereof; alternatively, the chemically-treated solid oxide can be selected from fluorided alumina, chlorided alumina, sulfated alumina, fluorided silica-alumina, chlorided silica-alumina, sulfated silica-alumina, fluorided silica-zirconia, sulfated silica-zirconia, or any combination thereof.

In one aspect, the chemically-treated solid oxide can comprise a solid inorganic oxide comprising oxygen and at least one element selected from Group 2, 3, 4, 5, 6, 7, 8, 9, 10, 11, 12, 13, 14, or 15 of the periodic table, or comprising oxygen and at least one element selected from the lanthanide or actinide elements; alternatively, the chemically-treated solid oxide can comprise a solid inorganic oxide comprising oxygen and at least one element selected from Group 4, 5, 6, 12, 13, or 14 of the periodic table, or comprising oxygen and at least one element selected from the lanthanide elements. (See: *Hawley's Condensed Chemical Dictionary*, 11$^{th}$ Ed., John Wiley & Sons; 1995; Cotton, F. A.; Wilkinson, G.; Murillo; C. A.; and Bochmann; M. *Advanced Inorganic Chemistry*, 6$^{th}$ Ed., Wiley-Interscience, 1999.) Usually, the inorganic oxide can comprise oxygen and at least one element selected from Al, B, Be, Bi, Cd, Co, Cr, Cu, Fe, Ga, La, Mn, Mo, Ni, Sb, Si, Sn, Sr, Th, Ti, V, W, P, Y, Zn or Zr; alternatively, the inorganic oxide can comprise oxygen and at least one element selected from Al, B, Si, Ti, P, Zn or Zr.

Suitable examples of solid oxide materials or compounds that can be used in the chemically-treated solid oxide of the present disclosure include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof; alternatively, suitable examples of solid oxide materials or compounds that can be used in the chemically-treated solid oxide of the present disclosure include, but are not limited to, $Al_2O_3$, $B_2O_3$, $SiO_2$, $SnO_2$, $TiO_2$, $V_2O_5$, $WO_3$, $Y_2O_3$, ZnO, $ZrO_2$, and the like, including mixed oxides thereof, and combinations thereof; alternatively, suitable examples of solid oxide materials or compounds that can be used in the chemically-treated solid oxide of the present disclosure include, but are not limited to, $Al_2O_3$, $SiO_2$, $TiO_2$, $ZrO_2$, and the like, including mixed oxides thereof, and combinations thereof.

Examples of mixed oxides that can be used in the polyanionic solid of the present disclosure include, but are not limited to, silica-alumina, silica-titania, silica-zirconia, zeolites, clay minerals, silica-coated alumina, aluminum phosphate, aluminophosphate, heteropolytungstate, mullite, boehmite, alumina-titania, alumina-zirconia, zinc-aluminate and the like; alternatively, examples of mixed oxides that can be used in the polyanionic solid of the present disclosure include, but are not limited to, silica-alumina, silica-titania, silica-zirconia, alumina-titania, alumina-zirconia, zinc-aluminate and the like; alternatively, examples of mixed oxides that can be used in the polyanionic solid of the present disclosure include, but are not limited to, silica-alumina, silica-titania, silica-zirconia, alumina-titania, and the like.

In one aspect of this disclosure, the solid oxide material is chemically-treated by contacting it with at least one electron-withdrawing component, typically an electron-withdrawing anion source. Further, the solid oxide material can be chemically-treated with a metal ion if desired, then calcining to form a metal-containing or metal-impregnated chemically-treated solid oxide. Alternatively, a solid oxide material and an electron-withdrawing anion source are contacted and calcined simultaneously. The method by which the oxide is contacted with an electron-withdrawing component, typically a salt or an acid of an electron-withdrawing anion, includes, but is not limited to, gelling, co-gelling, impregnation of one compound onto another, and the like. Typically, following any contacting method, the contacted mixture of oxide compound, electron-withdrawing anion, and the metal ion if present can be calcined.

Without being bound by theory, the electron-withdrawing component used to treat the oxide can be any component that increases the Lewis or Brønsted acidity of the solid oxide upon treatment. In one aspect, the electron-withdrawing component is an electron-withdrawing anion derived from a salt, an acid, or other compound such as a volatile organic compound that may serve as a source or precursor for that anion. Examples of electron-withdrawing anions include, but are not limited to, sulfate, bisulfate, fluoride, chloride, bromide, iodide, fluoro sulfate, fluoroborate, phosphate, fluorophosphate, trifluoroacetate, triflate, fluorozirconate, fluorotitanate, trifluoroacetate, triflate, and the like, including mixtures and combinations thereof; alternatively, examples of electron-withdrawing anions include, but are not limited to, sulfate, bisulfate, fluoride, chloride, fluoro sulfate, fluoroborate, phosphate, fluorophosphate, trifluoroacetate, triflate, fluorozirconate, fluorotitanate, and the like, including mixtures and combinations thereof; alternatively, examples of electron-withdrawing anions include, but are not limited to, fluoride, sources of fluoride, chloride, bisulfate, sulfate, and the like, including mixtures and combinations thereof. In addition, other ionic or non-ionic compounds that serve as sources for these electron-withdrawing anions may also be employed in the present disclosure.

When the electron-withdrawing component can comprise a salt of an electron-withdrawing anion, the counterion or cation of that salt may be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, H$^+$, [H(OEt$_2$)$_2$]$^+$, and the like; alternatively, ammonium; alternatively, trialkyl ammonium; alternatively, tetraalkyl ammonium; alternatively, tetraalkyl phosphonium; or alternatively, H$^+$, [H(OEt$_2$)$_2$]$^+$.

Further, combinations of one or more different electron withdrawing anions, in varying proportions, can be used to tailor the specific activity of the chemically-treated solid oxide to the desired level. Combinations of electron withdrawing components may be contacted with the oxide material simultaneously or individually, and any order that affords the desired chemically-treated solid oxide acidity. For example, one aspect of this disclosure is employing two or more electron-withdrawing anion source compounds in two or more separate contacting steps. Thus, one example of such a process by which an chemically-treated solid oxide is prepared is as follows: a selected solid oxide compound, or combination of oxide compounds, is contacted with a first electron-withdrawing anion source compound to form a first mixture, this first mixture is then calcined, the calcined first mixture is then contacted with a second electron-withdrawing anion source compound to form a second mixture, followed by calcining said second mixture to form a treated solid oxide compound. In such a process, the first and second electron-withdrawing anion source compounds are typically different compounds, although they may be the same compound.

In one aspect of the disclosure, the chemically-treated solid oxide may be produced by a process comprising:
1) contacting a solid oxide compound with at least one electron-withdrawing anion source compound to form a first mixture; and
2) calcining the first mixture to form the chemically-treated solid oxide.

In another aspect of this disclosure, the chemically-treated solid oxide can be produced by a process comprising:
1) contacting at least one solid oxide compound with a first electron-withdrawing anion source compound to form a first mixture; and
2) calcining the first mixture to produce a calcined first mixture;
3) contacting the calcined first mixture with a second electron-withdrawing anion source compound to form a second mixture; and
4) calcining the second mixture to form the chemically-treated solid oxide.

Thus, the solid oxide activator-support is sometimes referred to simply as a treated solid oxide compound.

In one aspect of this disclosure, once the solid oxide has been treated and dried, it may be subsequently calcined. Calcining of the chemically treated solid oxide is generally conducted in an ambient atmosphere; alternatively, in a dry ambient atmosphere. The solid oxide may be calcined at a temperature from about 200° C. to about 900° C.; alternatively, from about 300° C. to about 800° C.; alternatively, from about 400° C. to about 700° C.; or alternatively, from about 350° C. to about 550° C. The period of time at which the solid oxide is maintained at the calcining temperature may be about 1 minute to about 100 hours; alternatively, from about 1 hour to about 50 hours; alternatively, from about 3 hours to about 20 hours; or alternatively, from about 1 to about 10 hours.

Further, any type of suitable ambient atmosphere can be used during calcining. Generally, calcining is conducted in an oxidizing atmosphere, such as air. Alternatively, an inert atmosphere, such as nitrogen or argon, or a reducing atmosphere such as hydrogen or carbon monoxide, may be used.

In another aspect of the disclosure, the solid oxide component used to prepare the chemically-treated solid oxide has a pore volume greater than about 0.1 cc/g. In another aspect, the solid oxide component has a pore volume greater than about 0.5 cc/g, and in yet another aspect, greater than about 1.0 cc/g. In still another aspect, the solid oxide component has a surface area from about 100 to about 1000 $m^2/g$. In another aspect, solid oxide component has a surface area from about 200 to about 800 $m^2/g$, and in still another aspect, from about 250 to about 600 $m^2/g$.

The solid oxide material may be treated with a source of halide ion or sulfate ion, or a combination of anions, and optionally treated with a metal ion, then calcined to provide the chemically-treated solid oxide in the form of a particulate solid. In one aspect, the solid oxide material is treated with a source of sulfate, termed a sulfating agent, a source of chloride ion, termed a chloriding agent, a source of fluoride ion, termed a fluoriding agent, or a combination thereof, and calcined to provide the solid oxide activator.

In one aspect of this disclosure, the chemically-treated solid oxide can comprise a fluorided solid oxide in the form of a particulate solid, thus a source of fluoride ion is added to the oxide by treatment with a fluoriding agent. In still another aspect, fluoride ion may be added to the oxide by forming a slurry of the oxide in a suitable solvent such as alcohol or water, including, but are not limited to, the one to three carbon alcohols because of their volatility and low surface tension. Examples of fluoriding agents that can be used in this disclosure include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4$)$_2SiF_6$), ammonium hexafluorophosphate ($NH_4PF_6$), analogs thereof, and combinations thereof; alternatively, hydrofluoric acid (HF), ammonium fluoride ($NH_4F$), ammonium bifluoride ($NH_4HF_2$), ammonium tetrafluoroborate ($NH_4BF_4$), analogs thereof, and combinations thereof. For example, ammonium bifluoride $NH_4HF_2$ may be used as the fluoriding agent, due to its ease of use and ready availability.

In another aspect of the present disclosure, the solid oxide can be treated with a fluoriding agent during the calcining step. Any fluoriding agent capable of thoroughly contacting the solid oxide during the calcining step can be used. For example, in addition to those fluoriding agents described previously, volatile organic fluoriding agents may be used. Examples of volatile organic fluoriding agents useful in this aspect of the disclosure include, but are not limited to, freons, perfluorohexane, perfluorobenzene, fluoromethane, trifluoroethanol, and combinations thereof. Gaseous hydrogen fluoride or fluorine itself can also be used with the solid oxide is fluorided during calcining. One convenient method of contacting the solid oxide with the fluoriding agent is to vaporize a fluoriding agent into a gas stream used to fluidize the solid oxide during calcination.

Similarly, in another aspect of this disclosure, the chemically-treated solid oxide can comprise a chlorided solid oxide in the form of a particulate solid, thus a source of chloride ion is added to the oxide by treatment with a chloriding agent. The chloride ion may be added to the oxide by forming a slurry of the oxide in a suitable solvent. In another aspect of the present disclosure, the solid oxide can be treated with a chloriding agent during the calcining step. Any chloriding agent capable of serving as a source of chloride and thoroughly contacting the oxide during the calcining step can be used. For example, volatile organic choriding agents may be used. Examples of volatile organic choriding agents useful in this aspect of the disclosure include, but are not limited to, certain freons, perchlorobenzene, chloromethane, dichloromethane, chloroform, carbon tetrachloride, trichloroethanol, or any combination thereof. Gaseous hydrogen chloride or chlorine itself can also be used with the solid oxide during calcining. One convenient method of contacting the oxide with the chloriding agent is to vaporize a chloriding agent into a gas stream used to fluidize the solid oxide during calcination.

In one aspect, the amount of fluoride or chloride ion present before calcining the solid oxide is generally from about 2 to about 50% by weight, where the weight percents are based on the weight of the solid oxide, for example silica-alumina, before calcining. In another aspect, the amount of fluoride or chloride ion present before calcining the solid oxide is from about 3 to about 25% by weight, and in another aspect, from about 4 to about 20% by weight. Once impregnated with halide, the halided oxide may be dried by any method known in the art including, but not limited to, suction filtration followed by evaporation, drying under vacuum, spray drying, and the like, although it is also possible to initiate the calcining step immediately without drying the impregnated solid oxide.

In an aspect, silica-alumina may be utilized as the solid oxide material. The silica-alumina used to prepare the treated silica-alumina can have a pore volume greater than about 0.5 cc/g. In one aspect, the pore volume may be greater than about 0.8 cc/g, and in another aspect, the pore volume may be greater than about 1.0 cc/g. Further, the silica-alumina may have a surface area greater than about 100 m$^2$/g. In one aspect, the surface area is greater than about 250 m$^2$/g, and in another aspect, the surface area may be greater than about 350 m$^2$/g. Generally, the silica-alumina of this disclosure has an alumina content from about 5 to about 95%. In one aspect, the alumina content of the silica-alumina may be from about 5 to about 50%, and in another aspect, the alumina content of the silica-alumina may be from about 8% to about 30% alumina by weight. In yet another aspect, the solid oxide component can comprise alumina without silica and in another aspect, the solid oxide component can comprise silica without alumina.

The sulfated solid oxide can comprise sulfate and a solid oxide component such as alumina or silica-alumina, in the form of a particulate solid. The sulfated oxide can be further treated with a metal ion if desired such that the calcined sulfated oxide can comprise a metal. In one aspect, the sulfated solid oxide can comprise sulfate and alumina. In one aspect of this disclosure, the sulfated alumina is formed by a process wherein the alumina is treated with a sulfate source, for example selected from, but not limited to, sulfuric acid or a sulfate salt such as ammonium sulfate. In one aspect, this process may be performed by forming a slurry of the alumina in a suitable solvent such as alcohol or water, in which the desired concentration of the sulfating agent has been added. Suitable organic solvents include, but are not limited to, the one to three carbon alcohols because of their volatility and low surface tension.

In one aspect of the disclosure, the amount of sulfate ion present before calcining is generally from about 0.5 parts by weight to about 100 parts by weight sulfate ion to about 100 parts by weight solid oxide. In another aspect, the amount of sulfate ion present before calcining is generally from about 1 part by weight to about 50 parts by weight sulfate ion to about 100 parts by weight solid oxide, and in still another aspect, from about 5 parts by weight to about 30 parts by weight sulfate ion to about 100 parts by weight solid oxide. These weight ratios are based on the weight of the solid oxide before calcining. Once impregnated with sulfate, the sulfated oxide may be dried by any method known in the art including, but not limited to, suction filtration followed by evaporation, drying under vacuum, spray drying, and the like, although it is also possible to initiate the calcining step immediately.

In addition to being treated with an electron-withdrawing component (for example, halide or sulfate ion), the solid inorganic oxide of this disclosure can be treated with a metal source if desired, including metal salts or metal-containing compounds. In one aspect of the disclosure, these compounds may be added to or impregnated onto the solid oxide in solution form, and subsequently converted into the supported metal upon calcining. The solid oxide may be treated with metal salts or metal-containing compounds before, after, or at the same time that the solid oxide is treated with the electron-withdrawing anion.

Further, any method of impregnating the solid oxide material with a metal may be used. The method by which the oxide is contacted with a metal source, typically a salt or metal-containing compound, includes, but is not limited to, gelling, co-gelling, impregnation of one compound onto another, and the like. Following any contacting method, the contacted mixture of oxide compound, electron-withdrawing anion, and the metal ion is typically calcined. Alternatively, a solid oxide material, an electron-withdrawing anion source, and the metal salt or metal-containing compound are contacted and calcined simultaneously.

Various processes to prepare solid oxide activator-supports that can be employed in this disclosure have been reported. For example, U.S. Pat. Nos. 6,107,230, 6,165,929, 6,294,494, 6,300,271, 6,316,553, 6,355,594, 6,376,415, 6,391,816, 6,395,666, 6,524,987, 6,548,441, 6,750,302, 6,831,141, 6,936,667, 6,992,032, 7,601,665, 7,026,494, 7,148,298, 7,470,758, 7,517,939, 7,576,163, 7,294,599, 7,629,284, 7,501,372, 7,041,617, 7,226,886, 7,199,073, 7,312,283, 7,619,047, 7,884,163, 8,703,886, and 9,023,959 describe such methods, each of which is incorporated by reference herein, in pertinent part.

Organic Base on Solid Support as Polyanionic Solids

In one aspect, this disclosure encompasses a continuous process as described herein, in which the polyanionic solid (also termed an activator or co-catalyst) can comprise an organic base on a solid support. In this aspect, for example, the polyanionic solid can comprise, consists of, consists essentially of, or be selected from an organic base moiety immobilized on a solid support. For example, the organic base moiety immobilized on a solid support comprises structural units having the general formula (I):

SS-[A]$_x$-L-B    (I);

wherein SS is a solid support, A is an anchor moiety, L is a direct bond or linking moiety, and B is an organic base moiety, and wherein x is 0 to 3. In an aspect, the organic base moiety B has the general formula:

wherein each of R$^1$ and R$^2$, independently or together, are selected from H or an unbranched or branched, acyclic or cyclic, C$_1$-C$_{12}$ hydrocarbyl residue; and R$^3$ is selected independently from hydrogen or a substituted or an unsubstituted C$_1$-C$_{12}$ hydrocarbyl. Each of R$^1$ and R$^2$, independently or together, can be selected from H, methyl, ethyl, 1-propyl, 2-propyl, 1-butyl, 2-butyl, tert-butyl, 1-(2-methyl) propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, or xylyl.

In a further aspect, the organic base moiety B of the general formula SS-[A]$_x$-L-B (I) can have the formula:

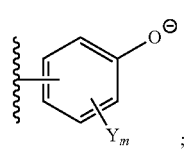

wherein Y is selected from a halide or a $C_1$-$C_6$ hydrocarbyl, and m is 0-4; and wherein ⸹ is the SS-[A]$_x$-L portion of formula (I).

According to this aspect, the organic base moiety immobilized on a solid support can have the following structure:

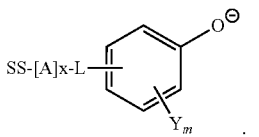

According to a further aspect, the organic base moiety B of the general formula SS-[A]$_x$-L-B (I) can have the formula:

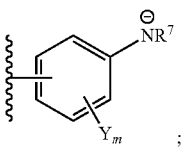

wherein Y is selected from a halide or a $C_1$-$C_6$ hydrocarbyl, m is 0-4, and $R^6$ is selected from a $C_1$-$C_6$ alkyl or aryl; and wherein ⸹ is the SS-[A]$_x$-L portion of formula (I).

According to this aspect, the organic base moiety immobilized on a solid support can have the following structure:

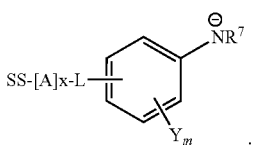

In a further aspect of the continuous process according to this disclosure, the organic base moiety immobilized on a solid support can have the general formula (II):

SS—[O]$_{3-n}$—Si(OR$^4$)$_n$—B   (II);

wherein n is 0, 1, or 2, and each $R^4$ is selected independently from a substituted or an unsubstituted $C_1$-$C_{12}$ hydrocarbyl.

The continuous process can also encompass use of an organic base immobilized on a solid support which can comprise structural units having the general formula (I):

SS-[A]$_x$-L-B   (I);

wherein the organic base moiety B is selected from [—CR$^1$R$^2$—O]$^-$, [—CR$^1$R$^2$—S]$^-$, [—CR$^1$R$^2$—NR$^3$]$^-$, or [—CR$^1$R$^2$—PR$^3$]$^-$, wherein each of $R^1$ and $R^2$, independently or together, are selected from H or an unbranched or branched, acyclic or cyclic, $C_1$-$C_{12}$ hydrocarbyl residue; and $R^3$ is selected independently from hydrogen or a substituted or an unsubstituted $C_1$-$C_{12}$ hydrocarbyl; and A is selected from [—YR$^5$R$^6$—CH$_2$], wherein a) Y is N$^+$ or C, and $R^5$ and $R^6$ are selected independently from hydrogen, or a substituted or an unsubstituted $C_1$-$C_{12}$ hydrocarbyl, or b) Y is Si, and $R^5$ and $R^6$ are selected independently from a substituted or an unsubstituted $C_1$-$C_{12}$ hydrocarbyl, or a substituted or an unsubstituted $C_1$-$C_{12}$ hydrocarbyloxide.

A further aspect is that combinations of any of these organic base moieties immobilized on at least one solid support are encompassed by this disclosure.

Metal Acrylate Release and Polyanionic Solid Regeneration

In the example of Scheme 1, the polyanionic solid can be a metal poly(4-vinylphenoxide), which is formed upon the reaction of the neutral polymer 5, for example poly(4-vinylphenol), with a base 7 such as a metal-containing base. For example, the metal in a metal-containing base can be, but is not limited to, a metal of Groups 1, 2, 12 or 13, such as lithium, sodium, potassium, rubidium, cesium, magnesium, calcium, zinc, aluminum or gallium. As illustrated in Scheme 1, the reaction of the polyanionic solid 3 and metalalactone 2 (for example, through an intermediate represented generally as 4) both eliminates or releases the metal acrylate 6 from 4 and regenerates catalyst compound 1 and byproduct neutral polymer 5 (e.g. poly(4-vinylphenol) in Scheme 1), which is regenerated to the polyanionic solid reactant upon its reaction with a regenerative base 7. Various bases 7 can be used according to this disclosure.

The step of regenerating the polyanionic solid can be effected by contacting the polyanionic solid with a regenerative base 7 comprising a metal cation following the formation of the α,β-unsaturated carboxylic acid or a salt thereof. A wide range of bases 7 can be used for this regeneration step. For example, the regenerative base 7 can be or can comprise metal-containing bases which can include any reactive inorganic basic metal compound or mixture of compounds that contain metal cations or cation sources, for example, alkali and alkaline earth metal compounds such as oxides, hydroxides, alkoxides, aryloxides, amides, alkyl amides, arylamides, and carbonates. Suitable bases include or comprise, for example, carbonates (e.g., Na$_2$CO$_3$, Cs$_2$CO$_3$, MgCO$_3$), hydroxides (e.g., Mg(OH)$_2$, Ca(OH)$_2$, NaOH, KOH), alkoxides (e.g., Al(O$^i$Pr)$_3$, Na(O$^t$Bu), Mg(OEt)$_2$), aryloxides (e.g. Na(OC$_6$H$_5$), sodium phenoxide) and the like. Typically, this regeneration step further comprising or is followed by the step of washing the polyanionic solid with a solvent or the diluent.

According to an aspect, the regenerative base 7 can be or can comprise a nucleophilic base, for example a metal hydroxide or metal alkoxide. While the regenerative base 7 can comprise a non-nucleophilic base, the processes disclosed herein work in the absence of a non-nucleophilic base such an alkali metal hydride or an alkaline earth metal hydride, an alkali metal or alkaline earth metal dialkylamides and diarylamides, an alkali metal or alkaline earth metal hexalkyldisilazane, and an alkali metal or alkaline earth metal dialkylphosphides and diarylphosphides.

Typically, the inorganic bases such as alkali metal hydroxides or alkali metal alkoxides have been found to work the best. However, in one aspect, the reaction of Scheme 1 can be conducted using some bases but in the absence of certain other organic bases such as an alkoxide, aryloxide, amide, alkyl amide, arylamide, or the like. In another aspect, the polyanionic solid (and associated cations) can be used and regenerated in the absence of an alkoxide or aryloxide. Further, the reactions and processes disclosed herein can be conducted in the absence of an alkoxide, an aryloxide, an alkylamide, an arylamide, an amine, a hydride, a phosphazene, and/or substituted analogs thereof. For example, the processes disclosed herein can be conducted in the absence of sodium hydride, an aryloxide salt (such as a sodium aryloxide), an alkoxide salt (such as a sodium tert-butoxide), and/or a phosphazene.

Diluents

The processes disclosed herein typically are conducted in the presence of a diluent. Mixtures and combinations of diluents can be utilized in these processes. The diluent can comprise, consist essentially of, or consist of, any suitable solvent or any solvent disclosed herein, unless otherwise specified. For example, the diluent can comprise, consist essentially of, or consist of a non-protic solvent, a protic solvent, a non-coordinating solvent, or a coordinating solvent. For instance, in accordance with one aspect of this disclosure, the diluent can comprise a non-protic solvent. Representative and non-limiting examples of non-protic solvents can include tetrahydrofuran (THF), 2,5-Me$_2$THF, acetone, toluene, chlorobenzene, pyridine, acetonitrile, carbon dioxide, olefin and the like, as well as combinations thereof. In accordance with another aspect, the diluent can comprise a weakly coordinating or non-coordinating solvent. Representative and non-limiting examples of weakly coordinating or non-coordinating solvents can include toluene, chlorobenzene, paraffins, halogenated paraffins, and the like, as well as combinations thereof.

In accordance with yet another aspect, the diluent can comprise a carbonyl-containing solvent, for instance, ketones, esters, amides, and the like, as well as combinations thereof. Representative and non-limiting examples of carbonyl-containing solvents can include acetone, ethyl methyl ketone, ethyl acetate, propyl acetate, butyl acetate, isobutyl isobutyrate, methyl lactate, ethyl lactate, N,N-dimethylformamide, and the like, as well as combinations thereof. In still another aspect, the diluent can comprise THF, 2,5-Me$_2$THF, methanol, acetone, toluene, chlorobenzene, pyridine, anisole, or a combination thereof; alternatively, THF; alternatively, 2,5-Me$_2$THF; alternatively, methanol; alternatively, acetone; alternatively, toluene; alternatively, chlorobenzene; or alternatively, pyridine.

In an aspect, the diluent can comprise (or consist essentially of, or consist of) an aromatic hydrocarbon solvent. Non-limiting examples of suitable aromatic hydrocarbon solvents that can be utilized singly or in any combination include benzene, toluene, xylene (inclusive of ortho-xylene, meta-xylene, para-xylene, or mixtures thereof), and ethylbenzene, or combinations thereof; alternatively, benzene; alternatively, toluene; alternatively, xylene; or alternatively, ethylbenzene.

In an aspect, the diluent can comprise (or consist essentially of, or consist of) a halogenated aromatic hydrocarbon solvent. Non-limiting examples of suitable halogenated aromatic hydrocarbon solvents that can be utilized singly or in any combination include chlorobenzene, dichlorobenzene, and combinations thereof; alternatively, chlorobenzene; or alternatively, dichlorobenzene.

In an aspect, the diluent can comprise (or consist essentially of, or consist of) an ether solvent. Non-limiting examples of suitable ether solvents that can be utilized singly or in any combination include dimethyl ether, diethyl ether, diisopropyl ether, di-n-propyl ether, di-n-butyl ether, diphenyl ether, methyl ethyl ether, methyl t-butyl ether, dihydrofuran, tetrahydrofuran (THF), 2,5-Me$_2$THF, 1,2-dimethoxyethane, 1,4-dioxane, anisole, and combinations thereof; alternatively, diethyl ether, dibutyl ether, THF, 2,5-Me$_2$THF, 1,2-dimethoxyethane, 1,4-dioxane, and combinations thereof; alternatively, THF; or alternatively, diethyl ether.

In a further aspect, any of these aforementioned diluents can be excluded from the diluent or diluent mixture. For example, the diluent can be absent a phenol or a substituted phenol, an alcohol or a substituted alcohol, an amine or a substituted amine, water, an ether, an aliphatic hydrocarbon solvent, an aromatic hydrocarbon solvent, an aldehyde or ketone, an ester or amide, and/or absent a halogenated aromatic hydrocarbon, or any substituted analogs of these diluents halogenated analogs, including any of the aforementioned diluents. Therefore, Applicant reserves the right to exclude any of the diluents provided herein.

The diluent can comprise carbon dioxide, and can also comprise CO$_2$ under pressure. The diluent also can comprise the α,β-unsaturated carboxylic acid or the salt thereof, formed in the process. The diluent can comprise any suitable non-protic solvent, any non-protic solvent disclosed herein, and/or carbon dioxide (CO$_2$) under pressure. The diluent can comprise any suitable non-protic solvent, any non-protic solvent disclosed herein, the olefin such as ethylene, and/or carbon dioxide (CO$_2$) under pressure. Specifically, the diluent can comprise the olefin such as ethylene and carbon dioxide (CO$_2$) under pressure. The diluent also can comprise any suitable weakly coordinating or non-coordinating solvent, or any weakly coordinating or non-coordinating solvent disclosed herein.

In all aspects and embodiments disclosed herein, the diluent can include or comprise carbon dioxide, olefin, or combinations thereof. At least a portion of the diluent can comprise the α,β-unsaturated carboxylic acid or the salt thereof, formed in the process.

Transition Metal Compounds and Ligands

In this disclosure, the term transition metal precursor, transition metal compound, transition metal catalyst, transition metal precursor compound, carboxylation catalyst, transition metal precursor complex and similar terms refer to a chemical compound that serves as the precursor to the metalalactone, prior to the coupling of the olefin and carbon dioxide at the metal center of the transition metal precursor compound. Therefore, the metal of the transition metal precursor compound and the metal of the metalalactone are the same. In some aspects, some of the ligands of the transition metal precursor compound carry over and are retained by the metalalactone following the coupling reaction. In other aspects, the transition metal precursor compound loses its existing ligands, referred to herein as first ligands, in presence of additional ligands such as chelating ligands, referred to herein as second ligands, as the metalalactone is formed. Therefore, the metalalactone generally incorporates the second (added) ligand(s), though in some aspects, the metalalactone can comprise the first ligand(s) that were bound in the transition metal precursor compound.

According to an aspect, the transition metal catalyst or compound used in the processes can be used without being immobilized on a solid support. That is the transition metal catalyst can be used is its usual form which is soluble in most useful solvents, without being bonded to or supported on any insoluble support, such as an inorganic oxide or mixed oxide material.

A prototypical example of a transition metal precursor compound that loses its initial ligands in the coupling reaction in the presence of a second (added) ligand, wherein the metalalactone incorporates the second (added) ligand(s), is contacting Ni(COD)$_2$ (COD is 1,5-cyclooctadiene) with a diphosphine ligand such as 1,2-bis(dicyclohexylphosphino) ethane in a diluent in the presence of ethylene and CO$_2$ to form a nickelalactone with a coordinated 1,2-bis(dicyclohexylphosphino)ethane bidentate ligand.

Accordingly, in an aspect, the process for producing an α,β-unsaturated carboxylic acid or a salt thereof, can comprise (1) contacting in any order: (a) a transition metal precursor compound comprising at least one first ligand; (b) optionally, at least one second ligand; (c) an olefin; (d) carbon dioxide ($CO_2$); (e) a diluent; and (f) an polyanionic solid comprising associated metal cations to provide a reaction mixture; and (2) applying reaction conditions to the reaction mixture suitable to form the α,β-unsaturated carboxylic acid or a salt thereof.

Generally, the processes disclosed herein employ a metalalactone or a transition metal precursor compound or complex. The transition metal of the metalalactone, or of the transition metal precursor compound, can be a Group 3 to Group 8 transition metal or, alternatively, a Group 8 to Group 11 transition metal. In one aspect, for instance, the transition metal can be Fe, Co, Ni, Cu, Ru, Rh, Pd, Ag, Ir, Pt, or Au, while in another aspect, the transition metal can be Fe, Ni, or Rh. Alternatively, the transition metal can be Fe; alternatively, the transition metal can be Co; alternatively, the transition metal can be Ni; alternatively, the transition metal can be Cu; alternatively, the transition metal can be Ru; alternatively, the transition metal can be Rh; alternatively, the transition metal can be Pd; alternatively, the transition metal can be Ag; alternatively, the transition metal can be Ir; alternatively, the transition metal can be Pt; or alternatively, the transition metal can be Au.

In particular aspects contemplated herein, the transition metal can be Ni. Hence, the metalalactone can be a nickelalactone and the transition metal precursor compound can be a Ni-ligand complex in these aspects.

The ligand of the metalalactone and/or of the transition metal precursor compound, can be any suitable neutral electron donor group and/or Lewis base. For instance, the suitable neutral ligands can include sigma-donor solvents that contain a coordinating atom (or atoms) that can coordinate to the transition metal of the metalalactone (or of the transition metal precursor compound). Examples of suitable coordinating atoms in the ligands can include, but are not limited to, O, N, S, and P, or combinations of these atoms. In some aspects consistent with this disclosure, the ligand can be a bidentate ligand.

In an aspect, the ligand used to form the metalalactone and/or the transition metal precursor compound can be an ether, an organic carbonyl, a thioether, an amine, a nitrile, or a phosphine. In another aspect, the ligand used to form the metalalactone or the transition metal precursor compound can be an acyclic ether, a cyclic ether, an acyclic organic carbonyl, a cyclic organic carbonyl, an acyclic thioether, a cyclic thioether, a nitrile, an acyclic amine, a cyclic amine, an acyclic phosphine, or a cyclic phosphine.

Suitable ethers can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable organic carbonyls can include ketones, aldehydes, esters, and amides, either alone or in combination, and illustrative examples can include, but are not limited to, acetone, acetophenone, benzophenone, N,N-dimethylformamide, N,N-dimethylacetamide, methyl acetate, ethyl acetate, and the like, including substituted derivatives thereof.

Suitable thioethers can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles can include, but are not limited to, acetonitrile, propionitrile, butyronitrile, benzonitrile, 4-methylbenzonitrile, and the like, including substituted derivatives thereof.

Suitable amines can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, 2,2'-bipyridine, 1,8-Diazabicyclo[5.4.0]undec-7-ene, di(2-pyridyl)dimethylsilane, N,N,N',N'-tetramethylethylenediamine, 1,10-phenanthroline, 2,9-dimethyl-1,10-phenanthroline, glyoxal-bis(mesityl)-1,2-diimine and the like, including substituted derivatives thereof. Suitable amines can be primary amines, secondary amines, or tertiary amines.

Suitable phosphines and other phosphorus compounds can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino)biphenyl, (S)-(+)-(3,5-dioxa-4-phospha-cyclohepta[2,1-a;3,4-a'] dinaphthalen-4-yl)dimethylamine, 2-(diphenylphosphino)-2'-methoxy-1,1'-binaphthyl, 1,2,3,4,5-pentaphenyl-1'-(di-t-butylphosphino)ferrocene, 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino)ethane, 1,2-bis(dicyclohexylphosphino)ethane, 1,3-bis(dicyclohexylphosphino)propane, 1,3-bis(diisopropylphosphino)propane, 1,3-bis(diphenylphosphino)propane, 1,3-bis(di-t-butylphosphino)propane, 1,4-bis(diisopropylphosphino)butane, 1,4-bis(diphenylphosphino)butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, 2-t-butylphosphinomethylpyridine, bis (diphenylphosphino)ferrocene, bis(diphenylphosphino)methane, bis(dicyclohexylphosphino)methane, bis(di-t-butylphosphino)methane, and the like, including substituted derivatives thereof.

In other aspects, the ligand used to form the metalalactone or the transition metal precursor compound can be a carbene, for example, a N-heterocyclic carbene (NHC) compound. Representative and non-limiting examples of suitable N-heterocyclic carbene (NHC) materials include the following:

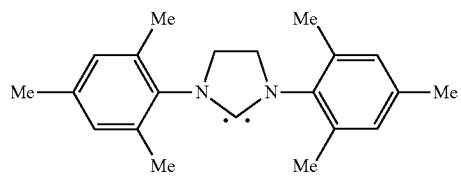

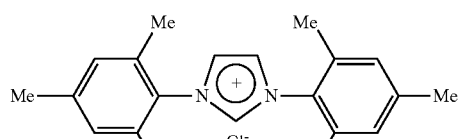

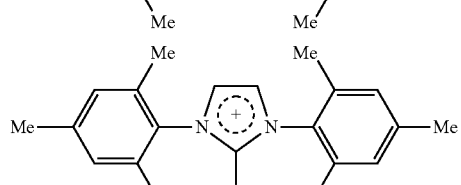

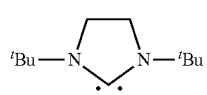

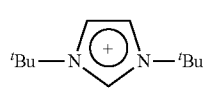

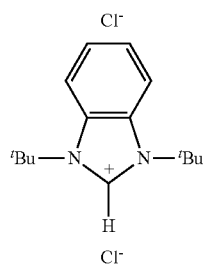

Illustrative and non-limiting examples of metalalactone complexes (representative nickelalactones) suitable for use as described herein include the following compounds (Cy=cyclohexyl, $^t$Bu=tert-butyl):

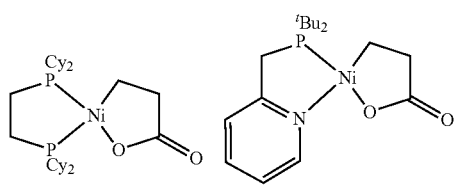

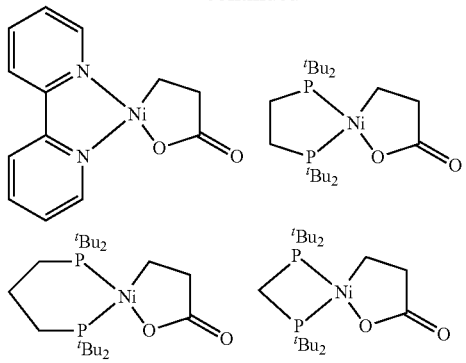

The transition metal precursor compounds corresponding to these illustrative metalalactones are shown below:

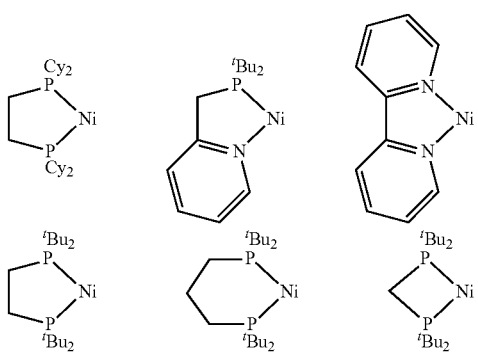

Metalalactones can be synthesized according to the following general reaction scheme (illustrated with nickel as the transition metal; Ni(COD)$_2$ is bis(1,5-cyclooctadiene)nickel(0)):

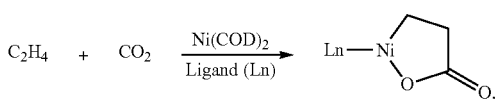

and according to suitable procedures well known to those of skill in the art.

Suitable ligands, transition metal precursor compounds, and metalalactones are not limited solely to those ligands, transition metal precursor compounds, and metalalactones disclosed herein. Other suitable ligands, transition metal precursor compounds, and metalalactones are described, for example, in U.S. Pat. Nos. 7,250,510, 8,642,803, and 8,697,909; Journal of Organometallic Chemistry, 1983, 251, C51-053; Z. Anorg. Allg. Chem., 1989, 577, 111-114; Journal of Organometallic Chemistry, 2004, 689, 2952-2962; Organometallics, 2004, Vol. 23, 5252-5259; Chem. Commun., 2006, 2510-2512; Organometallics, 2010, Vol. 29, 2199-2202; Chem. Eur. J., 2012, 18, 14017-14025; Organometallics, 2013, 32 (7), 2152-2159; and Chem. Eur. J., 2014, Vol. 20, 11, 3205-3211; the disclosures of which are incorporated herein by reference in their entirety.

The following references provide information related to the structure and/or activity relationships in the olefin and CO$_2$ coupling process, as observed by changes in phenoxide structure, the phosphine ligand structure, and other ligand structures: Manzini, S.; Huguet, N.; Trapp, O.; Schaub, T. Eur. J. Org. Chem. 2015, 7122; and Al-Ghamdi, M.; Vummaleti, S. V. C.; Falivene, L.; Pasha, F. A.; Beetstra, D. J.; Cavallo, L. Organometallics 2017, 36, 1107-1112. These references are incorporated herein by reference in their entireties.

Generally, the features of the processes disclosed herein (e.g., the metalalactone, the diluent, the polyanionic solid, the α,β-unsaturated carboxylic acid or salt thereof, the transition metal precursor compound, the olefin, and the reaction conditions under which the α,β-unsaturated carboxylic acid, or a salt thereof, is formed, among others) are independently described, and these features can be combined in any combination to further describe the disclosed processes.

Continuous Process and Reaction Methods

This disclosure provides a continuous process for producing an α,β-unsaturated carboxylic acid or salt thereof. In an aspect, the continuous process for producing an α,β-unsaturated carboxylic acid or salt thereof, the process can comprise:
1) in a first stage, contacting (a) a transition metal precursor compound comprising at least one first ligand, (b) optionally, at least one second ligand, (c) an olefin, (d) carbon dioxide ($CO_2$), and (e) a diluent to form a first composition; and
2) in a second stage, contacting a polyanionic solid with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid.

In this aspect, the first composition can comprise a metalalactone in which the metalalactone can comprise at least one ligand. In this aspect, and while not bound by theory, it is thought that in the second stage, the second composition formed upon contacting the polyanionic solid with the first composition can comprise an adduct of a metalalactone and the polyanionic solid.

This disclosure also provides a continuous process for producing an α,β-unsaturated carboxylic acid or salt thereof, the process comprising
1) in a first stage, obtaining or providing a first composition comprising a metalalactone compound and a diluent;
2) in a second stage, contacting a polyanionic solid with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid.

In this aspect as well, in the second stage, it is thought that the second composition formed upon contacting the polyanionic solid with the first composition can comprises an adduct of the metalalactone and the polyanionic solid.

In the continuous process according to this disclosure, the step of contacting the second composition with the polar solvent in the third stage to form the reacted solid can be carried out before contacting the reacted solid with the metal-containing base. In an aspect, contacting the second composition with the polar solvent in the third stage to form the reacted solid also can be carried out at the same time as contacting the reacted solid with the metal-containing base.

In the third stage of the continuous process of this disclosure, contacting the second composition with a polar solvent to release a metal salt of an α,β-unsaturated carboxylic acid and form a reacted solid can be carried out with any polar solvent. At least one polar protic solvent, at least one polar aprotic solvent, or combinations thereof can be used to release the metal salt of an α,β-unsaturated carboxylic acid. For example, any of the aforementioned diluents that are polar solvents can be employed. In an aspect, the polar solvent can comprise or can be selected from water, aliphatic alcohols, acetonitrile, pyridine, aromatic alcohols, ketones, aldehydes, esters, amides, halogenated solvents, ethers, and the like. In a further aspect, any of these aforementioned diluents can be excluded from the polar solvent or mixture of polar solvents that are used. Therefore, Applicant reserves the right to exclude any of the diluents provided herein.

Figure 2:
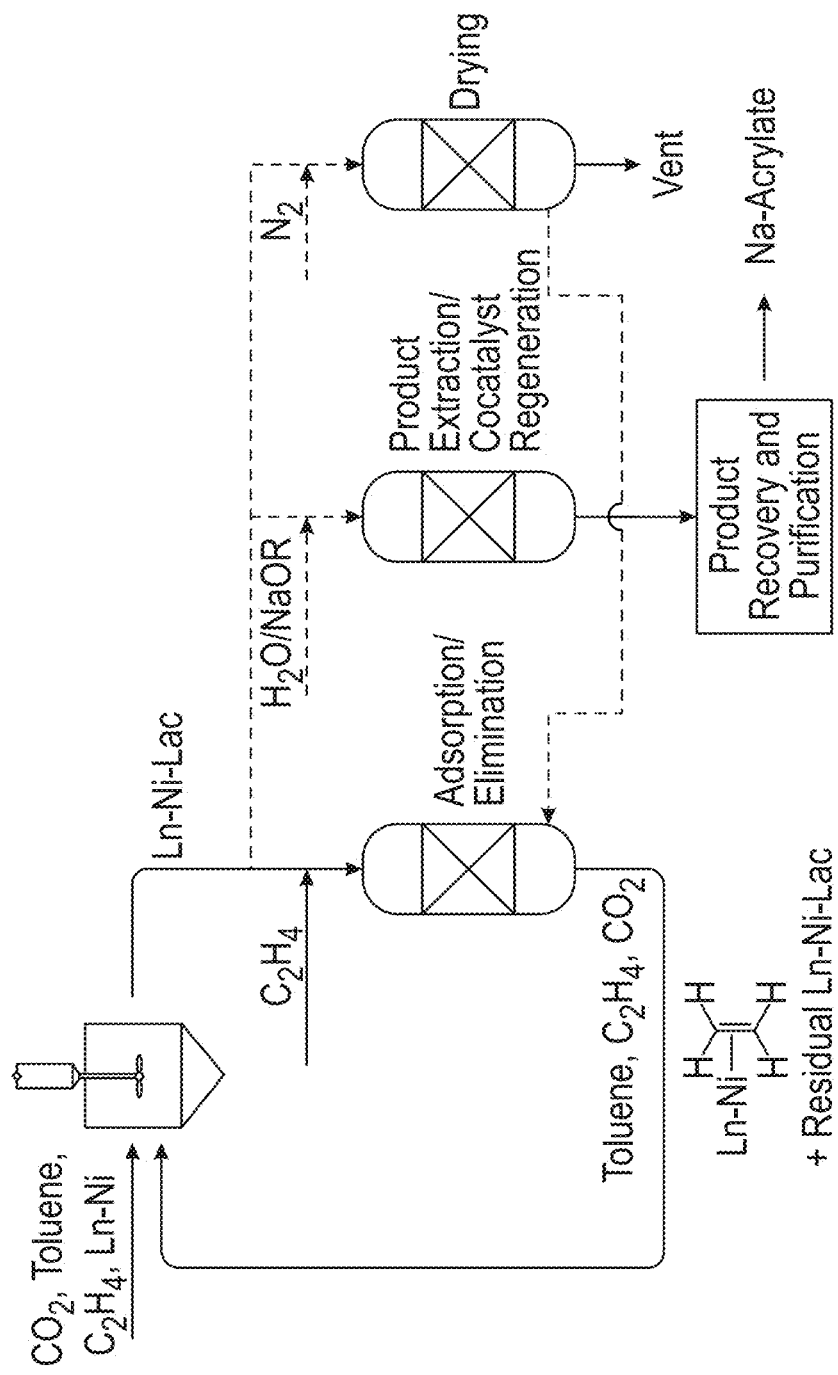
FIG. 2. illustrates certain conceptual aspects of the process, showing the concept for a continuous process for producing an α,β-unsaturated carboxylic acid or salt thereof based upon the reaction process of FIG. 1. For example.

FIG. 2. illustrates an aspect of this disclosure, showing a conceptual illustration of a continuous process for producing an α,β-unsaturated carboxylic acid or salt thereof based upon the reaction process shown in FIG. 1. This FIG. 2 schematic illustrates 1) a first stage in which a nickel precursor compound comprising at least one first ligand (Ln-Ni), optionally, at least one second ligand (also generically represented as Ln), ethylene, carbon dioxide ($CO_2$), and toluene (a diluent) are combined to form a first composition which includes a nickelalactone; 2) a second absorption/elimination stage, in which a polyanionic solid (also termed cocatalyst or activator) is contacted with the first composition to form a second composition, which can include an adduct of the nickelalactone and the polyanionic solid; and 3) a third stage in which (a) the second composition (typically comprising the nickelalactone-polyanionic solid adduct) is contacted with a polar solvent to release a metal salt of an α,β-unsaturated carboxylic acid and form a reacted solid, and (b) reacted solid (cocatalyst) is contacted with a metal-containing base to produce a regenerated polyanionic solid. FIG. 2 also illustrates an optional fourth stage in which the regenerated polyanionic solid is dried or partially dried. Regarding FIG. 2, this figures is not presented as a complete diagram or schematic of the process with transfer lines, valves and the like being shown. Rather, FIG. 2 is a conceptual illustration of aspects of the process. As an example, the three fixed bed reactors shown in FIG. 2 are simple illustrations of the three stages and selected portions of the pipes and the like that are specifically related to that stage.

Thus, in an aspect of the continuous process according to this disclosure, the second stage and the third stage can be carried out: a) concurrently in a second reactor and a third reactor, respectively; or b) sequentially in a single reactor. In another aspect, the first stage, the second stage, and the third stage are carried out simultaneously in a first reactor, a second reactor, and a third reactor, respectively. As demonstrated in the general scheme of FIG. 1, the first stage and first reactor of the continuous process are generally very different from the other stages and reactors. For example, there is generally a liquid transfer from the first stage/first reactor to the second stage/second reactor, because the transition metal complex which can comprise a metalalactone is transferred in a diluent to the second stage/second reactor, where contact with the polyanionic solid occurs. In principle, the second stage and the third stage of this continuous process can be carried out: a) concurrently in a second reactor and a third reactor, respectively; or alternatively, b) sequentially in a single reactor. Thus, in an aspect, the polyanionic solid is generally insoluble in the diluent.

Moreover, the continuous process according to this disclosure can further comprise, in a fourth stage, drying or partially drying the regenerated polyanionic solid. In principle, when the fourth stage is present in the continuous process, the second stage, the third stage, and the fourth stage can be carried out: a) concurrently in a second reactor, a third reactor, and a fourth reactor, respectively; or alternatively, b) sequentially in a single reactor. It is also possible to carry out, for example, the second stage and the third stage in one reactor, and transfer the resulting material to another reactor to carry out the fourth, drying stage.

With reference to FIG. 1 and FIG. 2, as provided further in this disclosure, the continuous process disclosed herein can comprise a step of contacting a transition metal precursor compound comprising at least one first ligand, an olefin, and carbon dioxide ($CO_2$) to form the metalalactone compound. That is, at least one ligand of the transition metal precursor compound can be carried over to the metalalactone compound. In further aspects, the process can further comprise a step of contacting a transition metal precursor compound comprising at least one first ligand with at least one second ligand, an olefin, and carbon dioxide ($CO_2$) to form the metalalactone compound. In this aspect, the ligand set of the metalalactone typically comprises the at least one ligand in addition to the metalalactone moiety. That is, the metalalactone compound can comprise the at least one first ligand, the at least one second ligand, or a combination thereof. In an aspect, for example, a transition metal precursor compound can be $Ni(COD)_2$, and one suitable second ligand can be a diphosphine ligand, and the metalalactone compound can comprise the nickelalactone moiety and the diphosphine ligand.

In some aspects, a first stage includes obtaining or providing a first composition comprising a metalalactone compound and a diluent, and in a second stage, the a polyanionic solid is contacted with the first composition comprising the metalalactone to form a second composition. These contacting steps can involve contacting, in any order, the metalalactone, the diluent, and the polyanionic solid, and additional unrecited materials. Likewise, additional materials or features can be employed in the third stage where the second composition is contacted with a polar solvent to release a metal salt of an $\alpha,\beta$-unsaturated carboxylic acid and form a reacted solid, and the reacted solid is contacting with a metal-containing base to produce a regenerated polyanionic solid. Further, it is contemplated that the continuous processes for producing an $\alpha,\beta$-unsaturated carboxylic acid or a salt thereof by a metalalactone elimination reaction can employ more than one metalalactone and/or more than one polyanionic solid. Additionally, a mixture or combination of two or more diluents can be employed.

According to an aspect, the polyanionic solid used in the continuous process can comprise a fixed bed. The polyanionic solid used in the continuous process can be formed onto beads or be supported on an inorganic or organic carrier material. Any suitable reactor, vessel, or container can be used in the recited stages, and as described herein, a single vessel can be used in more than one stage, for example, stage two and stage three. Non-limiting examples of the polyanionic solid can include a flow reactor, a fixed bed reactor, a moving reactor bed, and a stirred tank reactor. In particular aspects consistent with this disclosure, the metalalactone and the diluent can contact a fixed bed of the polyanionic solid, for instance, in a suitable vessel, such as in a continuous fixed bed reactor. In further aspects, combinations of more than one polyanionic solid can be used, such as a mixed bed of a first polyanionic solid and a second polyanionic solid, or sequential beds of a first polyanionic solid and a second polyanionic solid. In these and other aspects, the feed stream can flow upward or downward through the fixed bed. For instance, the metalalactone and the diluent can contact the first polyanionic solid and then the second polyanionic solid in a downward flow orientation, and the reverse in an upward flow orientation. In a different aspect, the metalalactone and the polyanionic solid can be contacted by mixing or stirring in the diluent, for instance, in a suitable vessel, such as a stirred tank reactor.

In an aspect, the continuous process for producing an $\alpha,\beta$-unsaturated carboxylic acid or a salt thereof can include forming an adduct of the metalalactone and the polyanionic solid and its associated metal cations. Without intending to be bound by theory, there is some interaction between the metalalactone and the polyanionic solid and its associated metal cations that are believed to destabilize the metalalactone for its elimination of the metal acrylate. This interaction can be referred to generally as an adduct of the metalalactone and the polyanionic solid or an adduct of the $\alpha,\beta$-unsaturated carboxylic acid with the polyanionic solid. This adduct can contain all or a portion of the $\alpha,\beta$-unsaturated carboxylic acid and can be inclusive of salts of the $\alpha,\beta$-unsaturated carboxylic acid.

The continuous process disclosed herein involves applying reaction conditions to a reaction mixture suitable to form an $\alpha,\beta$-unsaturated carboxylic acid or a salt thereof, for example, subjecting the second composition, which may include an adduct of the metalalactone and the polyanionic solid, to chemical reagent or reaction conditions or treatment that produce the $\alpha,\beta$-unsaturated carboxylic acid or its salt. Various methods can be used to liberate the $\alpha,\beta$-unsaturated carboxylic acid or its salt, from the combination of the second composition. In one aspect, for instance, this contacting occurs in a third stage, which can comprise contacting the second composition, which may include an adduct of the metalalactone and the polyanionic solid, with an acid. Representative and non-limiting examples of suitable acids can include HCl, acetic acid, and the like, as well as combinations thereof. In another aspect, this stage can comprise contacting the second composition with a base. Representative and non-limiting examples of suitable bases can include carbonates (e.g., $Na_2CO_3$, $Cs_2CO_3$, $MgCO_3$), hydroxides (e.g., $Mg(OH)_2$, $Na(OH)$, alkoxides (e.g., $Al(O^iPr)_3$, $Na(O^tBu)$, $Mg(OEt)_2$), and the like, as well as combinations thereof ($^iPr$=isopropyl, $^tBu$=tert-butyl, Et=ethyl). In yet another aspect, the third stage can comprise contacting the second composition with a suitable solvent. Representative and non-limiting examples of suitable solvents can include carbonyl-containing solvents such as ketones, esters, amides, etc. (e.g., acetone, ethyl acetate, N,N-dimethylformamide, etc., as described herein above), alcohol solvents, water, and the like, as well as combinations thereof.

In an aspect of the continuous process of this disclosure, the contacting step of the third stage further comprises heating the second composition to any suitable temperature. That is, the release of the $\alpha,\beta$-unsaturated carboxylic acid or its salt can comprise heating the adduct of the metalalactone and the polyanionic solid and its associated metal cations to any suitable temperature. This temperature can be in a range, for example, from 50 to 1000° C., from 100 to 800° C., from 150 to 600° C., from 250 to 1000° C., from 250° C. to 550° C., or from 150° C. to 500° C. The duration of heating is not limited to any particular period of time, as long of the period of time is sufficient to liberate the $\alpha,\beta$-unsaturated carboxylic acid from the polyanionic solid. As those of skill in the art recognize, the appropriate treating step depends upon several factors, such as the particular diluent used in the process, and the particular polyanionic solid used in the process, amongst other considerations. One further treatment step can comprise, for example, a workup step with additional olefin to displace an alkene-metal bound acrylate.

Illustrative and non-limiting examples of suitable olefins that can be used in the continuous process of this disclosure include, but are not limited to, ethylene, propylene, butene (e.g., 1-butene), pentene, hexene (e.g., 1-hexene), heptane, octene (e.g., 1-octene), and styrene and the like, as well as combinations thereof. In aspects of this process that utilize ethylene, the step of contacting a transition metal precursor compound with an olefin and carbon dioxide ($CO_2$) can be conducted using any suitable pressure of ethylene, or any pressure of ethylene disclosed herein, e.g., from 10 psig (70 KPa) to 1,000 psig (6,895 KPa), from 25 psig (172 KPa) to 500 psig (3,447 KPa), or from 50 psig (345 KPa) to 300 psig (2,068 KPa), and the like. Further, the olefin can be ethylene, and the step of contacting a transition metal precursor compound with an olefin and carbon dioxide ($CO_2$) can be conducted using a constant addition of the olefin, a constant addition of carbon dioxide, or a constant addition of both the olefin and carbon dioxide, to provide the reaction mixture. By way of example, in a process wherein the ethylene and carbon dioxide ($CO_2$) are constantly added, the process can utilize an ethylene:$CO_2$ molar ratio of from 5:1 to 1:5, from 3:1 to 1:3, from 2:1 to 1:2, or about 1:1, to provide the reaction mixture.

According to a further aspect of the above process that utilizes a transition metal precursor compound, the process can include the step of contacting a transition metal precursor compound with an olefin and carbon dioxide ($CO_2$) conducted using any suitable pressure of $CO_2$, or any pressure of $CO_2$ disclosed herein, e.g., from 20 psig (138 KPa) to 2,000 psig (13,790 KPa), from 50 psig (345 KPa) to 750 psig (5,171 KPa), or from 100 psig (689 KPa) to 300 psig (2,068 KPa), and the like. In any of the processes disclosed herein, the processes can further comprise a step of monitoring the concentration of at least one reaction mixture component, at least one elimination reaction product, or a combination thereof, for any reason, such as to adjust process parameters in real time, to determine extent or reaction, or to stop the reaction at the desired point.

As illustrated, this process that utilizes a transition metal precursor compound comprising at least one first ligand includes one aspect in which no second ligand is employed in the contacting step, and another aspect in which a second ligand is used in the contacting step. That is, one aspect involves the contacting step of the process comprising contacting the transition metal precursor compound comprising at least one first ligand with the at least one second ligand. The order of contacting can be varied. For example, the contacting step of the process disclosed above can comprise contacting (a) the transition metal precursor compound comprising at least one first ligand with (b) the at least one second ligand to form a pre-contacted mixture, followed by contacting the pre-contacted mixture with the remaining components (c)-(f) in any order to provide the reaction mixture.

In further aspects related to the stages of the continuous process, the contacting step of the first stage which uses a transition metal precursor can further comprise contacting the transition metal precursor compound comprising at least one first ligand with the at least one second ligand, that is, at least one second ligand is employed. In an aspect, the contacting step of the first stage can comprise contacting (a) the transition metal precursor compound with (b) the at least one second ligand to form a pre-contacted mixture, followed by contacting the pre-contacted mixture with (c) the olefin, (d) carbon dioxide ($CO_2$), and (e) the diluent to form the first composition. Moreover, the contacting step of the first stage can comprise contacting the components (a)-(e) in any order.

In the continuous process of this disclosure, the contacting step of the second stage can comprise contacting the polyanionic solid with a second diluent to form a mixture, followed by contacting the mixture with the first composition to form the second composition.

In an aspect of the continuous process, the contacting step in the third stage can further comprise contacting an additive selected from an acid, a base, or a reductant. For example, the contacting step of the third stage further comprises contacting the second composition with any suitable acid, or any acid disclosed herein, e.g., HCl, acetic acid, and the like. In an aspect, the contacting step of the third stage may further comprise contacting the second composition with any suitable solvent, or any solvent disclosed herein, e.g., carbonyl-containing solvents such as ketones, esters, amides, etc. (e.g., acetone, ethyl acetate, N,N-dimethylformamide), alcohols, water, and the like.

The continuous process according to this disclosure can further comprise a step of isolating the α,β-unsaturated carboxylic acid, or the salt thereof, e.g., using any suitable separation/purification procedure or any separation/purification procedure disclosed herein, e.g., evaporation, distillation, chromatography, and the like.

As above, any suitable reactor, vessel, or container can be used to contact the transition metal-ligand, olefin, diluent, polyanionic solid, and carbon dioxide, whether using a fixed bed of the polyanionic solid, a stirred tank for contacting (or mixing), or some other reactor configuration and process. While not wishing to be bound by the following theory, a proposed and illustrative reaction scheme for this process is provided below.

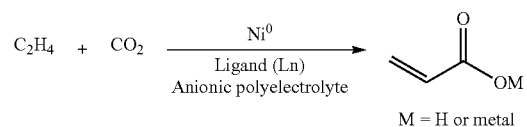

M = H or metal

Independently, the contacting and forming steps of any of the processes disclosed herein (i.e., for performing a metalalactone elimination reaction, for producing an α,β-unsaturated carboxylic acid, or a salt thereof), can be conducted at a variety of temperatures, pressures, and time periods. For instance, the temperature at which the components in step (1) are initially contacted can be the same as, or different from, the temperature at which the forming step (2) is performed. As an illustrative example, in the contacting step, the components can be contacted initially at temperature T1 and, after this initial combining, the temperature can be increased to a temperature T2 for the forming step (e.g., to form the α,β-unsaturated carboxylic acid, or the salt thereof). Likewise, the pressure can be different in the contacting step and the forming step. Often, the time period in the contacting step can be referred to as the contact time, while the time period in forming step can be referred to as the reaction time. The contact time and the reaction time can be, and often are, different.

In an aspect, the contacting step and/or the forming step of the processes disclosed herein, that is, the contacting step in any one or more of the first stage, the second stage, and/or the third stage, can be conducted at a temperature in a range from 0° C. to 250° C.; alternatively, from 20° C. to 200° C.; alternatively, from 0° C. to 95° C.; alternatively, from 10° C. to 75° C.; alternatively, from 10° C. to 50° C.; or alternatively, from 15° C. to 70° C. In these and other aspects, after the initial contacting, the temperature can be changed, if desired, to another temperature for the forming step. These temperature ranges also are meant to encompass circumstances where the contacting step and/or the forming step can be conducted at a series of different temperatures, instead of at a single fixed temperature, falling within the respective ranges.

In an aspect, the contacting step and/or the forming step of the processes disclosed herein, for example, the contacting step in any one or more of the first stage, the second stage, and/or the third stage, can be conducted at a pressure in a range from 5 (34 KPa) to 10,000 psig (68,948 KPa), such as, for example, from 5 psig (34 KPa) to 2500 psig (17,237 KPa). In some aspects, the pressure can be in a range from 5 psig (34 KPa) to 500 psig (3,447 KPa); alternatively, from 25 psig (172 KPa) to 3000 psig (20,684 KPa); alternatively, from 45 psig (310 KPa) to 1000 psig (6,895 KPa); or alternatively, from 50 psig (345 KPa) to 250 psig (1,724 KPa).

The contacting step of the processes is not limited to any particular duration of time. That is, the respective components can be initially contacted rapidly, or over a longer period of time, before commencing the forming step. Hence, the contacting step can be conducted, for example, in a time period ranging from as little as 1-30 seconds to as long as 1-12 hours, or more. In non-continuous or batch operations, the appropriate reaction time for the forming step can depend upon, for example, the reaction temperature, the reaction pressure, and the ratios of the respective components in the contacting step, among other variables. Generally, however, the forming step can occur over a time period that can be in a range from 1 minute to 96 hours, such as, for example, from 2 minutes to 96 hours, from 5 minutes to 72 hours, from 10 minutes to 72 hours, or from 15 minutes to 48 hours.

In the continuous process, the contacting step in any one or more of the second stage and/or the third stage can be conducted at any suitable weight hourly space velocity (WHSV) or any WHSV disclosed herein, e.g., from 0.05 to 50 hr$^{-1}$, from 1 to 25 hr$^{-1}$, from 1 to 5 hr$^{-1}$, etc., based on the amount of the polyanionic solid. Thus, the continuous process can be expressed in terms of weight hourly space velocity (WHSV)—the ratio of the weight of the metalalactone (or transition metal-ligand complex, or the total of the reaction solution containing the transition metal precursors, first ligands, second ligands, olefin, diluent, anionic polyelectrolyte, and carbon dioxide metal-ligand complex) which comes in contact with a given weight of anionic electrolyte per unit time (for example, hr$^{-1}$). While not limited thereto, the WHSV employed, based on the amount of the polyanionic solid, can be in a range from 0.05 to 100 hr$^{-1}$, from 0.05 to 50 hr$^{-1}$, from 0.075 to 50 hr$^{-1}$, from 0.1 to 25 hr$^{-1}$, from 0.5 to 10 hr$^{-1}$, from 1 to 25 hr$^{-1}$, or from 1 to 5 hr$^{-1}$.

In the processes disclosed herein, the molar yield of the $\alpha,\beta$-unsaturated carboxylic acid, or the salt thereof), based on the metalalactone (or the transition metal-ligand complex) is at least 2%, and more often can be at least 5%, at least 10%, or at least 15%. In particular aspects of this disclosure, the molar yield can be at least 18%, at least 20%, at least 25%, at least 35%, at least 50%, at least 60%, at least 75%, or at least 85%, or at least 90%, or at least 95%, or at least 100%. That is, catalytic formation of the $\alpha,\beta$-unsaturated carboxylic acid or the salt thereof can be effected with the disclosed system. For example, the molar yield of the $\alpha,\beta$-unsaturated carboxylic acid, or the salt thereof, based on the metalalactone or based on the transition metal precursor compound can be at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, or at least 500%.

The specific $\alpha,\beta$-unsaturated carboxylic acid (or salt thereof) that can be formed or produced using the processes of this disclosure is not particularly limited. Illustrative and non-limiting examples of the $\alpha,\beta$-unsaturated carboxylic acid can include acrylic acid, methacrylic acid, 2-ethylacrylic acid, cinnamic acid, and the like, as well as combinations thereof. Illustrative and non-limiting examples of the salt of the $\alpha,\beta$-unsaturated carboxylic acid can include sodium acrylate, potassium acrylate, lithium acrylate, magnesium acrylate, sodium (meth)acrylate, and the like, as well as combinations thereof.

Once formed, the $\alpha,\beta$-unsaturated carboxylic acid (or salt thereof) can be purified and/or isolated and/or separated using suitable techniques which can include, but are not limited to, evaporation, distillation, chromatography, crystallization, extraction, washing, decanting, filtering, drying, and the like, including combinations of more than one of these techniques. In an aspect, the process can for performing a metalalactone elimination reaction (or the process for producing an $\alpha,\beta$-unsaturated carboxylic acid, or a salt thereof) can further comprise a step of separating or isolating the $\alpha,\beta$-unsaturated carboxylic acid (or salt thereof) from other components, e.g., the diluent, the anionic electrolyte, and the like.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

General Considerations

Unless otherwise noted, all operations were performed under purified nitrogen or vacuum using standard Schlenk or glovebox techniques. Toluene (Honeywell) and tetrahydrofuran (Aldrich) was degassed and dried over activated 4 Å molecular sieves under nitrogen. Sodium tert-butoxide, potassium tert-butoxide, poly(4-vinylphenol) ($M_w$~11,000 g/mol), poly(4-vinylphenol-co-methyl(meth)acrylate) ($M_w$~8,000-12,000 g/mol), and brominated poly(4-vinylphenol) ($M_w$~5,800 g/mol) were purchased from Sigma-Aldrich and used as received. Phenol/formaldehyde resin was purchased as hollow beads (~5-127 μm) from Polysciences, Inc. Bis(1,5-cyclooctadiene)nickel(0) and 1,2-Bis (dicyclohexylphosphino)ethane were purchased from Strem and were used as received. (TMEDA)Ni(CH$_2$CH$_2$CO$_2$) was prepared according to literature procedures (Fischer, R; Nestler, B., and Schutz, H. *Z. anorg. allg. Chem.* 577 (1989) 111-114).

Preparation of Compounds

Sodium Poly(4-Vinylphenol). To sodium tert-butoxide (15 g, 125 mmol) and poly(4-vinylphenol) (12 g, 125 mmol)

was added toluene (600 mL) in a 1 L round-bottomed flask equipped with a stirbar. The mixture was stirred for four days then frit filtered. The filter cake was washed with 30 mL of toluene followed by 15 mL of toluene, then allowed to dry. The dry cake was washed with 3×20 mL of toluene leaving a solid.

Potassium Poly(4-Vinylphenol). Prepared analogously to sodium poly(4-vinylphenol) substituting potassium tert-butoxide for sodium tert-butoxide.

Sodium Poly(4-Vinylphenol-Co-Methyl(Meth)Acrylate). Prepared analogously to sodium poly(4-vinylphenol) substituting poly(4-vinylphenol-co-methyl(meth)acrylate) for poly(4-vinylphenol).

Sodium Poly(4-Vinylphenol), Brominated. Prepared analogously to sodium poly(4-vinylphenol) substituting poly(4-vinylphenol), brominated for poly(4-vinylphenol).

Sodium Phenol/Formaldehyde Resin. Phenolic resin (phenol/formaldehyde resin) was suspended in a solution of sodium hydroxide in either water or methanol and stirred at 55° C. overnight prior to filtration, and subsequently washed with copious amounts of the solvent in which it was treated. The solid was then dried under vacuum prior to storage under nitrogen.

TABLE 1

Ethylene/carbon dioxide coupling and acrylate yields

| Example | M | Solvent | [Solvent] (mL) | [$C_2H_4$] (psi (KPa)) | [$CO_2$] (psi (KPa)) | Acrylate Yield (%) |
|---|---|---|---|---|---|---|
| 1 | Na | Toluene | 300 | 150 (1,034) | 100 (689) | 14 |
| 2 | K | Toluene | 300 | 100 (689) | 150 (1,034) | 68 |
| 3 | K | Toluene | 300 | 150 (1,034) | 300 (2,068) | 117 |
| 4 | K | Toluene | 50 | 150 (1,034) | 300 (2,068) | 42 |
| 5 | K | Toluene | 50 | 75 (517) | 300 (2,068) | 25 |
| 6 | Na | Toluene | 300 | 150 (1,034) | 300 (2,068) | 104 |
| 7 | Na[A] | Toluene | 300 | 150 (1,034) | 300 (2,068) | 130 |
| 8 | Na | Toluene | 50 | 150 (1,034) | 300 (2,068) | 23 |
| 9 | Na | THF | 50 | 150 (1,034) | 300 (2,068) | 52 |
| 10 | Na | THF | 300 | 150 (1,034) | 300 (2,068) | 62 |

[A] 2.00 g of poly(4-vinylphenoxide) were used in this example.

Examples 1-10

Experimental Procedure for Ethylene/Carbon Dioxide Coupling

The ethylene/carbon dioxide reaction of these examples is set out in reaction (1) below, and specific reagents, reaction conditions, and yields are set out in Table 1.

A 1-liter autoclave pressure reactor was charged with solvent followed by a combined mixture of Ni(COD)$_2$ (0.10 mmol), bis(dicyclohexylphosphino)ethane (0.11 mmol), and poly(4-vinylphenoxide) (1.00 g) in 10 mL of solvent. The reactor was set to 50° C., pressurized with ethylene at the desired level, and equilibrated for 5-10 minutes (min) prior to being pressurized and equilibrated with carbon dioxide. The reactor was then set to 100° C. and stirred for 6 hours. After this reaction time, and after cooling to ambient temperature, the reactor was slowly vented and the mixture was collected. The solvent was removed in vacuo and the residue was stirred in 10-20 mL of deuterium oxide for 30 min prior to the addition of a sorbic acid/acetone-$d_6$ solution. The mixture was filtered and analyzed by NMR (sorbic acid is used as the internal standard) for acrylate yield determination.

Examples 11-17

Experimental Procedure for Nickelalactone Conversion to Acrylate

To study the elimination step of the disclosed process, the efficiencies of various alkoxides or aryloxides for the conversion of a diphosphine-stabilized nickelalactone to acrylic acid were assessed. Specifically, the following experiments show the efficiencies of sodium and potassium (4-vinylphenoxide) for the conversion of an in situ prepared diphosphine-stabilized nickelalactone, and the data were compared to the conversion using molecular sodium tert-butoxide for acrylate formation from the analogous nickelalactones. The metalalactone to acrylate conversion reaction of these examples is set out in reaction (2) below, and specific reagents, reaction conditions, and yields are set out in Table 2. In reaction (2), the "metal alkoxide" includes the polymeric alkoxides shown in Table 2.

In a 10 mL vial, (TMEDA)Ni(CH$_2$CH$_2$CO$_2$) (0.018 mmol), bis(dicyclohexylphosphino)-ethane (0.018 mmol), poly(4-vinylphenoxide), and solvent (5 mL) were combined and stirred at 60° C. for 30-60 min. Following removal of solvent, the solid residue was taken up in D$_2$O (3-5 mL) for 30 min and filtered. An aliquot of a prepared sorbic acid/acetone-$d_6$ solution was added for determination of acrylic acid yield by NMR.

(1)

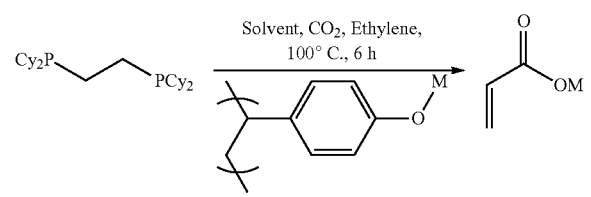

(2)

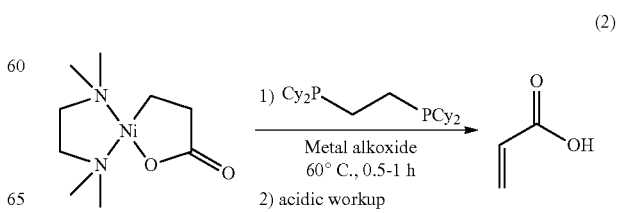

TABLE 2

Nickelalactone conversion to acrylate and acrylate yields

| Example | Metal Alkoxide | Solvent | [Metal Alkoxide] (mg) | % Yield |
|---|---|---|---|---|
| 11 | Sodium poly(4-vinylphenoxide) | Toluene | 100 | 33 |
| 12 | Sodium poly(4-vinylphenoxide) | Toluene | 250 | 32 |
| 13 | Sodium poly(4-vinylphenoxide) | Toluene | 25 | 15 |
| 14 | Potassium poly(4-vinylphenoxide) | Toluene | 100 | 24 |
| 15 | Sodium poly(4-vinylphenol-co-methyl(meth)acrylate) | Toluene | 100 | 66 |
| 16 | Sodium poly(4-vinylphenol), brominated | Toluene | 100 | 6 |
| 17 | Sodium tert-butoxide | THF | 7 | 16 |

The study from Table 2 reveals, among other things, that increasing the sodium poly(4-vinylphenoxide) amount from 100 mg to 250 mg (Examples 11 and 12) provides the same overall yield of the sodium acrylate/acrylic acid. Using the potassium salt (Example 14) as compared to the sodium salt (Example 11) of the poly(4-vinylphenoxide) somewhat lowered the yield of the sodium acrylate/acrylic acid.

Accordingly, this disclosure demonstrates at least the following: 1) a facile acid-base reaction that affords a metal polyvinylphenoxide or variants thereof in excellent yields with negligible byproducts; 2) a nickelalactone destabilization and cleavage that can proceed in surprisingly short time frames, that is, shorter times than expected (<1 hour); and 3) the increased loadings of metal polyvinylphenoxide does not diminish the resulting yield of the acrylate/acrylic acid.

Example 18

Polymeric Stationary Phases for Catalytic Acrylate Formation

The present disclosure also provides for using polymeric stationary phases, such as polyphenol resins (e.g. poly(4-vinylphenolate) resins) or polyaromatic resins (e.g. phenol-formaldehyde resins) in a column or other suitable solid state configuration, in which formation of the acrylate from a metalalactone (such as a nickelalactone) in a mobile phase can be effected.

FIG. 1 illustrates one way in which a polymeric stationary phase catalyst column can be configured, in which the coupling reaction and elution of the metal acrylate from the column can be carried out. As shown, a metal (e.g. sodium) poly(4-vinylphenolate) resins were found to be suitable polyanionic solid promoters or "co-catalysts" in the conversion of olefin/carbon dioxide-derived nickelalactone intermediates. This method can provide both easier separation of acrylate from other materials and ease of regeneration of the polymeric support materials to its salt form, such as sodium poly(4-vinylphenoxide).

Example 19-21

Sodium-Treated Crosslinked Polyaromatic Resins as Stoichiometric Co-Catalysts in Olefin/Carbon Dioxide Conversion to α,β-Unsaturated Carboxylates Because the metal (e.g. sodium) poly(4-vinylphenolate) resins were found to be suitable promoters and sources of cations in the conversion of olefin and carbon dioxide-derived nickelalactone intermediates, an evaluation of their crosslinked analogues was undertaken. It was believed that these crosslinked polyaromatic resins would be sufficiently insoluble in many commercial diluents to be applicability as a polymeric promoters and cation sources in a fixed bed/column reactor setting. This method further allows for the potential regeneration of the spent solid co-catalyst in both aqueous (for example, sodium hydroxide in water) and/or organic media (for example, sodium alkoxide in toluene).

The following reaction (3) illustrates the conversion reaction of an olefin and carbon dioxide-derived nickelalactone intermediate that was undertaken to evaluate some crosslinked polyelectrolyte analogues. Reaction conditions for reaction (3) are: 0.10 mmol [Ni], 0.11 mmol diphosphine ligand, 500 mL of toluene, 1.0 g of sodium-treated, crosslinked polyaromatic resin (solid activator). The reactor was equilibrated to 150 psi of ethylene followed by 300 psi of carbon dioxide prior to heating. The yield reported in Table 3 was determined by $^1$H NMR spectroscopy in a $D_2O/(CD_3)_2CO$ mixture relative to a sorbic acid standard.

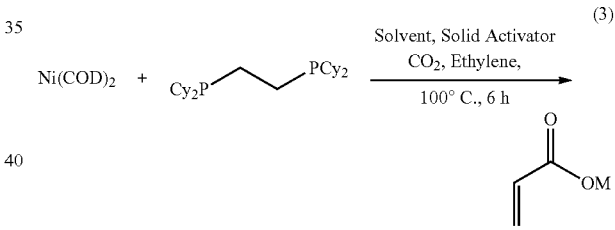

(3)

The following table describe various examples where commercial polyaromatic resins, which were either further treated with a sodium base under appropriate conditions or are commercially available in the sodium form, were found to be effective in the nickel-mediated synthesis of sodium acrylate from ethylene and carbon dioxide.

TABLE 3

Nickel-mediated conversion of carbon dioxide and ethylene to sodium acrylate with sodium treated polyaromatics.[A]

| Example | Solvent | Co-catalyst Solid | Base & Sodium Source | [Solid]:[Na] (wt) | Acrylate yield (%) |
|---|---|---|---|---|---|
| 19 | toluene | Phenol/Formaldehyde | NaOH (MeOH) | 0.3 | 1.8 |
| 20 | toluene | Phenol/Formaldehyde | NaOH (aq) | 0.3 | 6.0 |
| 21 | toluene | Phenol/Formaldehyde | NaO-t-Bu | 1.0 | n.d.[B] |

[A]Reaction Conditions: 0.10 mmol [Ni], 0.11 mmol diphosphine ligand, 500 mL toluene, 1.0 g solid activator (phenol-formaldehyde resin). Reactor was equilibrated to 150 psi ethylene followed by 300 psi carbon dioxide prior to heating. Yield determined by $^1$H NMR spectroscopy in $D_2O/(CD_3)_2CO$ mixture relative to sorbic acid standard.
[B]None detected.

Even though the yields of acrylate when employing these sodium-treated crosslinked resins may be modest, the data indicate that the nickel-mediated conversion of carbon dioxide and ethylene to sodium acrylate with sodium treated crosslinked polyaromatic resins can be carried out. Further, the insolubilities of these resins in many commercial solvents will allow for their utility in fixed bed/column configurations.

The phenol/formaldehyde resins can be treated with sodium hydroxide to produce what are believed to be sodium aryloxide sites that are active for promoting nickelalactone scission, and more so when the NaOH is dissolved in water to provide a higher solubility (Example 20) versus methanol (Example 19).

Example 21

Crosslinked Polyaromatic Resin Co-catalysts in Olefin/Carbon Dioxide Conversion to α,β-Unsaturated Carboxylates, Using Co-monomers In this example, co-monomer phenol compounds are used together with formaldehyde to prepare the crosslinked polyaromatic resins for use as described according to the disclosure. The resin was prepared using the co-monomer combination of resorcinol (m-dihydroxybenzene) and 2-fluorophenol monomer with formaldehyde, and the resulting resin was sodium-treated (NaOH, dissolved in water or alcohol) to generate the polyanionic solid, according to equation (4).

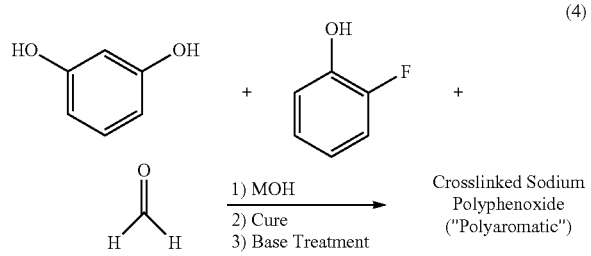

(4)

The polyaromatic resin is thought to act as a co-catalyst upon treatment with sodium hydroxide because of what are believed to be sodium aryloxide sites that promote nickelalactone scission. It is noted that increased crosslink density is obtained using longer drying times to remove trapped excess water.

Examples 22-25

Additional Stationary Phases for Catalytic Acrylate Formation

The present disclosure also provides for using other polymeric stationary phases and modifications thereof, for example, in a column or other suitable solid state configuration. Further variations of this technology include but are not limited to the following examples.

Example 22. Polymer modifications that include acid-base reaction being effected using a wide range of metal bases, including alkali and alkaline hydroxides, alkoxides, aryloxides, amides, alkyl or aryl amides, and the like, such that an assortment of electrophiles can be used in nickelalactone destabilization as demonstrated herein for the polyvinylphenols.

Example 23. Polymer modifications can also include using variants of the polyvinylphenol, that can be prepared by polymerization of hydroxyl-substituted styrenes having a variety of organic and inorganic substituents, such as alkyls, halogens, and heteroatom substituents.

Example 24. Polymer modifications can also include using co-polymers based on, for example, the co-polymerization of a protected hydroxyl-substituted styrene (such as acetoxystyrene) with other styrenes and (meth)acrylates (typically followed by hydrolysis to generate the polyvinylphenol co-polymer) to produce libraries of polymeric electrophiles.

Example 25. Polymer support variations are also envisioned, including for example polymers that can be supported onto beads or other surfaces. One class of polymer support variation that is envisioned is a cast polymer that can function as an ion exchange membrane.

Example 26-29

Chemically-Treated Solid Oxides as Co-catalysts in Olefin/Carbon Dioxide Conversion to α,β-Unsaturated Carboxylates The following examples demonstrate the utility of the chemically-treated solid oxides as co-catalyst for the olefin-$CO_2$ coupling reactions in acrylate formation. The chemically-treated solid oxides tested were sulfated alumina and fluorided silica-coated alumina.

When the polyanionic solid is a chemically treated solid oxide, preparing the chemically treated solid oxide initially involves calcining the chemically treated solid oxide to eliminate or greatly reduce water and to introduce the electron withdrawing anion, in this case, fluoride. However, the continuous process involve a regeneration of the polyanionic solids which can be effected by base treatment as described herein. The continuous process also involves a stage in which the second composition comprising the combination of the metal complex (such as metalalactone) and the polyanionic solid (such as a chemically treated solid oxide) are contacted with a polar solvent such as water to rinse and/or release a metal salt of an α,β-unsaturated carboxylic acid and form a reacted solid. Subsequent regeneration of the polyanionic solids is generally effected by base treatment, and a subsequent water wash can be used.

Therefore, the water reaction and subsequent regeneration of the polyanionic solid suggested that the regenerated co-catalyst solid may not be moisture-free. The following tests were conducted with the fluorided silica-coated alumina and sulfated alumina, including tests in which the fluorided silica-coated alumina and sulfated alumina were washed with water followed by treatment with sodium tert-butoxide, to re-generate the co-catalyst. These solids were screened for acrylate conversion efficacy versus their non-water washed analogs. The non-water washed analogs were completely water-free from calcination as well as base treatment in dry solvent. These examples are set out in the following reaction and the results are provided in the following table.

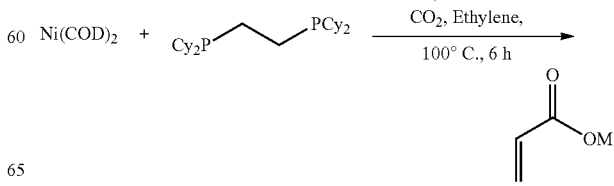

(5)

TABLE 4

Nickel-mediated conversion of carbon dioxide and ethylene to sodium acrylate with chemically treated solid oxides (SSAs).[A]

| Example | SSA Co-catalyst | Solvent | Acrylate yield (%) |
|---|---|---|---|
| 26 | NaO-t-Bu treated sulfated alumina | Toluene | 102 |
| 27 | NaO-t-Bu treated fluorided silica-coated alumina | Toluene | 131 |
| 28 | Sulfated alumina treated with water followed by NaO-t-Bu | Toluene | 350 |
| 29 | Fluorided silica-coated alumina treated by water followed by NaO-t-Bu | Toluene | 218 |

[A]Reaction Conditions: 0.10 mmol [Ni], 0.11 mmol diphosphine ligand, 500 mL solvent, 1.0 g SSA solid activator. Reactor was equilibrated to 150 psi ethylene followed by 300 psi carbon dioxide prior to heating. Extracted in to $D_2O$ for yield determined by $^1H$ NMR spectroscopy relative to sorbic acid standard.

The water-washed co-catalysts (Examples 28-29) were observed to produce substantially more acrylate than their non-water-washed analogs (Examples 26-27). These results were surprising because it was unexpected that aqueous regeneration would still support the activity of the co-catalyst, and especially surprising that the acrylate production was substantially better than the non-aqueous and dry co-catalyst examples.

The invention is described above with reference to numerous aspects and embodiments, and specific examples. Many variations will suggest themselves to those skilled in the art in light of the above detailed description. All such obvious variations are within the full intended scope of the appended claims. Other aspects of the invention can include, but are not limited to, the following Aspects. Many aspects are described as "comprising" certain components or steps, but alternatively, can "consist essentially of" or "consist of" those components or steps unless specifically stated otherwise.

Aspect 1. A continuous process for producing an α,β-unsaturated carboxylic acid or salt thereof, the process comprising
1) in a first stage, contacting (a) a transition metal precursor compound comprising at least one first ligand, (b) optionally, at least one second ligand, (c) an olefin, (d) carbon dioxide ($CO_2$), and (e) a diluent to form a first composition; and
2) in a second stage, contacting a polyanionic solid with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid.

Aspect 2. A continuous process for producing an α,β-unsaturated carboxylic acid or salt thereof, the process comprising
1) in a first stage, contacting (a) a transition metal precursor compound comprising at least one first ligand, (b) optionally, at least one second ligand, (c) an olefin, (d) carbon dioxide ($CO_2$), and (e) a diluent to form a first composition comprising a metalalactone compound; and
2) in a second stage, contacting a polyanionic solid with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid.

Aspect 3. A continuous process for producing an α,β-unsaturated carboxylic acid or salt thereof, the process comprising
1) in a first stage, obtaining or providing a first composition comprising a metalalactone compound and a diluent;
2) in a second stage, contacting a polyanionic solid with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid.

Aspect 4. A continuous process for producing an α,β-unsaturated carboxylic acid or salt thereof, the process comprising
1) in a first stage, obtaining or providing a first composition comprising a metalalactone compound and a diluent;
2) in a second stage, contacting a polyanionic solid with the first composition to form a second composition comprising an adduct of the metalalactone compound and the polyanionic solid; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid.

Aspect 5. A continuous process according to any one of Aspects 1-4, wherein contacting the second composition with the polar solvent in the third stage to form the reacted solid is carried out before contacting the reacted solid with the metal-containing base.

Aspect 6. A continuous process according to any one of Aspects 1-4, wherein contacting the second composition with the polar solvent in the third stage to form the reacted solid is carried out at the same time as contacting the reacted solid with the metal-containing base.

Aspect 7. A continuous process according to any one of Aspects 1-4, wherein the polar solvent comprises water, an aliphatic alcohol, an aromatic alcohol, an inorganic acid, an organic acid, or a combination thereof.

Aspect 8. A continuous process according to any one of Aspects 1-6, wherein:
the first stage and the second stage are carried out: a) concurrently in a first reactor and a second reactor, respectively; or b) sequentially in a single reactor; or
the second stage and the third stage are carried out: a) concurrently in a second reactor and a third reactor, respectively; or b) sequentially in a single reactor.

Aspect 9. A continuous process according to any one of Aspects 1-6, wherein the first stage, the second stage, and the third stage are carried out simultaneously in a first reactor, a second reactor, and a third reactor, respectively.

Aspect 10. A continuous process according to any one of Aspects 1-6, further comprising, in a fourth stage, drying or partially drying the regenerated polyanionic solid.

Aspect 11. A continuous process according to Aspect 10, wherein the second stage, the third stage, and the fourth stage are carried out: a) concurrently in a second reactor, a third reactor, and a fourth reactor, respectively; or b) sequentially in a single reactor.

Aspect 12. The process according to any of the preceding Aspects, wherein the polyanionic solid is insoluble in the diluent.

Aspect 13. The process according to Aspect 2, wherein the second composition comprises an adduct of the metalalactone compound and the polyanionic solid.

Aspect 14. A continuous process according to any one of Aspects 1-13, wherein the polyanionic solid comprises an alkoxide, an aryloxide, an acrylate, a (meth)acrylate, a sulfonate, an alkyl thiolate, an aryl thiolate, an alkyl amide, or an aryl amine group.

Aspect 15. A continuous process according to any one of Aspects 1-13, wherein the polyanionic solid comprises a poly(vinyl aryloxide), a poly(vinyl alkoxide), a poly(acrylate), a poly((meth)acrylate), a poly(styrene sulfonate), a phenol-formaldehyde resin, a polyhydroxyarene-formaldehyde resin (such as a resorcinol-formaldehyde resin), a polyhydroxyarene- and fluorophenol-formaldehyde resin (such as a resorcinol- and 2-fluorophenol-formaldehyde resin), a poly(vinylarylamide), a poly(vinyl alkylamide), or combinations thereof.

Aspect 16. A continuous process according to any one of Aspects 1-13, wherein the polyanionic solid comprises a poly(vinyl aryloxide), a poly(vinyl alkoxide), a substituted analog thereof, or a combination thereof.

Aspect 17. A continuous process according to any one of Aspects 1-13, wherein the polyanionic solid comprises sodium(poly-4-vinylphenoxide).

Aspect 18. A continuous process according to any one of Aspects 1-13, wherein the polyanionic solid comprises a phenol-formaldehyde resin, a polyhydroxyarene-formaldehyde resin (such as a resorcinol-formaldehyde resin), a polyhydroxyarene- and fluorophenol-formaldehyde resin (such as a resorcinol- and 2-fluorophenol-formaldehyde resin), or combinations thereof.

Aspect 19. A continuous process according to any one of Aspects 1-13, wherein the polyanionic solid comprises a phenol-formaldehyde resin, a resorcinol-formaldehyde resin, a resorcinol- and fluorophenol-formaldehyde resin, or combinations thereof.

Aspect 20. A continuous process according to any one of Aspects 1-13, wherein the polyanionic solid comprises a phenol-formaldehyde resin or a resorcinol- and 2-fluorophenol-formaldehyde resin.

Aspect 21. A continuous process according to any one of Aspects 1-13, wherein the polyanionic solid comprises a phenol-formaldehyde resin.

Aspect 22. A continuous process according to any one of Aspects 1-21, wherein the polyanionic solid comprises any suitable metal cation, any metal cation disclosed herein, any suitable Lewis acidic metal cation, or any Lewis acidic metal cation disclosed herein.

Aspect 23. A continuous process according to any one of Aspects 1-21, wherein the polyanionic solid comprises associated metal cations comprising or selected from an alkali metal, an alkaline earth metal, or a combination thereof.

Aspect 24. A continuous process according to any one of Aspects 1-21, wherein the polyanionic solid comprises associated metal cations comprising or selected from lithium, sodium, potassium, magnesium, calcium, strontium, barium, aluminum, or zinc.

Aspect 25. A continuous process according to any one of Aspects 1-21, wherein the polyanionic solid comprises associated metal cations comprising or selected from sodium or potassium.

Aspect 26. A continuous process according to any one of Aspects 1-13, wherein the polyanionic solid comprises a metal oxide.

Aspect 27. A continuous process according to any one of Aspects 1-13, wherein the polyanionic solid comprises a calcined metal oxide.

Aspect 28. A continuous process according to any one of Aspects 26-27, wherein the metal oxide comprises silica, alumina, silica-alumina, silica-coated alumina, aluminum phosphate, aluminophosphate, heteropolytungstate, mullite, titania, zirconia, magnesia, boria, zinc oxide, silica-titania, silica-zirconia, a mixed oxide thereof, or any mixture thereof.

Aspect 29. A continuous process according to any one of Aspects 1-13, wherein the polyanionic solid comprises a metal-treated sodium oxide.

Aspect 30. A continuous process according to any one of Aspects 1-13, wherein the polyanionic solid comprises a solid oxide that has been contacted with the metal-containing base.

Aspect 31. A continuous process according to any one of Aspects 1-13, wherein the polyanionic solid comprises a chemically-treated solid oxide that has been hydroxylated and subsequently contacted with the metal-containing base.

Aspect 32. A continuous process according to any one of Aspects 1-13, wherein the polyanionic solid comprises, consists of, consists essentially of, or is selected from a chemically-treated solid oxide comprising at least one solid oxide that has been treated with at least one electron withdrawing anion.

Aspect 33. A continuous process according to any one of Aspects 1-13, wherein the polyanionic solid comprises, consists of, consists essentially of, or is selected from a chemically-treated solid oxide, comprising:

at least one of silica, alumina, silica-alumina, silica-coated alumina, aluminum phosphate, aluminophosphate, heteropolytungstate, mullite, titania, zirconia, magnesia, boria, zinc oxide, silica-titania, silica-zirconia, a mixed oxide thereof, or any mixture thereof, that has been chemically treated with at least one electron withdrawing anion.

Aspect 34. A continuous process according to any one of Aspects 1-13, wherein the polyanionic solid comprises, consists of, consists essentially of, or is selected from a chemically-treated solid oxide, comprising:

at least one of silica, alumina, silica-alumina, silica-coated alumina, aluminum phosphate, aluminophosphate, heteropolytungstate, mullite, titania, zirconia, magnesia, boria, zinc oxide, silica-titania, silica-zirconia, a mixed oxide thereof, or any mixture thereof, that has been chemically treated with at least one electron withdrawing anion;

wherein the at least one electron withdrawing anion comprises fluoride, chloride, bromide, iodide, phosphate, triflate, trifluoroacetate, sulfate, bisulfate, fluorosulfate, fluoroborate, fluorophosphate, fluorozirconate, fluorotitanate, phosphotungstate, or any combination thereof.

Aspect 35. A continuous process according to any one of Aspects 32-34, wherein the chemically-treated solid oxide comprises at least one silica-coated alumina treated with at least one electron-withdrawing anion, wherein: the at least one silica-coated alumina has a weight ratio of alumina to silica in a range from about 1:1 to about 100:1, and the at least one electron-withdrawing anion comprises fluoride, chloride, bromide, phosphate, triflate, bisulfate, sulfate, or any combination thereof.

Aspect 36. A continuous process according to any one of Aspects 32-34, wherein the chemically-treated solid oxide comprises, consists of, consists essentially of, or is selected from fluorided alumina, chlorided alumina, bromided alumina, fluorided-chlorided alumina, sulfated alumina, fluorided silica-alumina, chlorided silica-alumina, bromided silica-alumina, fluorided-chlorided silica-alumina, sulfated silica-alumina, fluorided silica-titania, chlorided silica-titania, bromided silica-titania, fluorided-chlorided silica-titania, sulfated silica-titania, fluorided silica-zirconia, chlorided silica-zirconia, bromided silica-zirconia, fluorided-chlorided silica-zirconia, sulfated silica-zirconia, fluorided silica-coated alumina, chlorided silica-coated alumina, bromided silica-coated alumina, fluorided-chlorided silica-coated alumina, sulfated silica-coated alumina, fluorided mullite, chlorided mullite, bromided mullite, fluorided-chlorided mullite, or sulfated mullite.

Aspect 37. A continuous process according to any one of Aspects 32-34, wherein the chemically-treated solid oxide comprises, consists of, consists essentially of, or is selected from fluorided silica-alumina, fluorided-chlorided silica-alumina, sulfated silica-alumina, fluorided silica-coated alumina, fluorided-chlorided silica-coated alumina, a sulfated silica-coated alumina, fluorided mullite, fluorided-chlorided mullite, or sulfated mullite.

Aspect 38. A continuous process according to any one of Aspects 32-34, wherein the polyanionic solid comprises, consists essentially or, consists of, or is selected from a fluorided-chlorided silica-coated alumina, a fluorided silica-coated alumina, or a chlorided silica-coated alumina.

Aspect 39. A continuous process according to any one of Aspects 32-24, wherein the solid oxide comprises, consists of, consists essentially of, or is selected from alumina, silica, silica-alumina, silica-coated alumina, silica-titania, silica-zirconia, mullite, or any combination thereof.

Aspect 40. A continuous process according to any one of Aspects 32-39, wherein the silica-coated alumina comprises from about 10 to about 80 wt. % silica, based on the weight of the silica-coated alumina; the fluorided-chlorided silica-coated alumina comprises from about 2 to about 15 wt. % F, based on the weight of the fluorided-chlorided silica-coated alumina; and/or the fluorided-chlorided silica-coated alumina comprises from about 1 to about 10 wt. % Cl, based on the weight of the fluorided-chlorided silica-coated alumina.

Aspect 41. A continuous process according to any one of Aspects 36-38 and 40, wherein the fluorided-chlorided silica-coated alumina is produced by a process comprising: (a) calcining a silica-coated alumina at a peak calcining temperature to produce a calcined silica-coated alumina; (b) contacting the calcined silica-coated alumina with a chlorine-containing compound and calcining at a peak chloriding temperature to produce a chlorided silica-coated alumina; and (c) contacting the chlorided silica-coated alumina with a fluorine-containing compound and calcining at a peak fluoriding temperature to produce the fluorided-chlorided silica-coated alumina.

Aspect 42. A continuous process according to any one of Aspects 34-41, wherein the fluorided-chlorided silica-coated alumina has: a pore volume in a range from about 0.9 to about 2.0 mL/g; and a surface area in a range from about 200 to about 700 m²/g.

Aspect 43. A continuous process according to any one of Aspects 1-13, wherein the polyanionic solid comprises, consists of, consists essentially of, or is selected from an organic base moiety immobilized on a solid support.

Aspect 44. A continuous process according to Aspect 43, wherein the organic base moiety immobilized on a solid support comprises structural units having the general formula (I):

wherein SS is a solid support, A is an anchor moiety, L is a direct bond or linking moiety, and B is an organic base moiety, and wherein x is 0 to 3.

Aspect 45. A continuous process according to Aspect 44, wherein the organic base moiety B has the general formula:

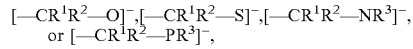

wherein each of $R^1$ and $R^2$, independently or together, are selected from H or an unbranched or branched, acyclic or cyclic, $C_1$-$C_{12}$ hydrocarbyl residue; and $R^3$ is selected independently from hydrogen or a substituted or an unsubstituted $C_1$-$C_{12}$ hydrocarbyl.

Aspect 46. A continuous process according to Aspect 45, wherein each of $R^1$ and $R^2$, independently or together, are selected from H, methyl, ethyl, 1-propyl, 2-propyl, 1-butyl, 2-butyl, tert-butyl, 1-(2-methyl) propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, or xylyl.

Aspect 47. A continuous process according to Aspect 44, wherein the organic base moiety B of the general formula SS-[A]$_x$-L-B (I) has the formula:

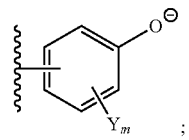

wherein Y is selected from a halide or a $C_1$-$C_6$ hydrocarbyl, and m is 0-4; and wherein ⸱ is the SS-[A]$_x$-L portion of formula (I).

According to this Aspect, the organic base moiety immobilized on a solid support has the following structure, as defined in these Aspects:

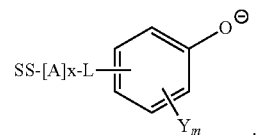

Aspect 48. A continuous process according to Aspect 44, wherein the organic base moiety B of the general formula SS-[A]$_x$-L-B (I) has the formula:

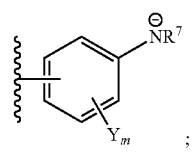

wherein Y is selected from a halide or a $C_1$-$C_6$ hydrocarbyl, m is 0-4, and $R^6$ is selected from a $C_1$-$C_6$ alkyl or aryl; and wherein ⦃ is the SS-[A]$_x$-L portion of formula (I).
According to this Aspect, the organic base moiety immobilized on a solid support has the following structure, as defined in these Aspects:

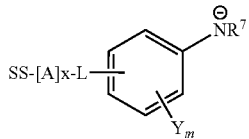

Aspect 49. A continuous process according to Aspect 43, wherein the organic base moiety immobilized on a solid support has the general formula (II):

wherein n is 0, 1, or 2, and each $R^4$ is selected independently from a substituted or an unsubstituted $C_1$-$C_{12}$ hydrocarbyl.

Aspect 50. A continuous process according to Aspect 43, wherein the organic base moiety immobilized on a solid support comprises structural units having the general formula (I):

wherein the organic base moiety B is selected from [—$CR^1R^2$—O]$^-$, [—$CR^1R^2$—S]$^-$, [—$CR^1R^2$—$NR^3$]$^-$, or [—$CR^1R^2$—$PR^3$]$^-$, wherein each of $R^1$ and $R^2$, independently or together, are selected from H or an unbranched or branched, acyclic or cyclic, $C_1$-$C_{12}$ hydrocarbyl residue; and $R^3$ is selected independently from hydrogen or a substituted or an unsubstituted $C_1$-$C_{12}$ hydrocarbyl; and A is selected from [—$YR^5R^6$—$CH_2$], wherein
a) Y is $N^+$ or C, and $R^5$ and $R^6$ are selected independently from hydrogen, or a substituted or an unsubstituted $C_1$-$C_{12}$ hydrocarbyl, or
b) Y is Si, and $R^5$ and $R^6$ are selected independently from a substituted or an unsubstituted $C_1$-$C_{12}$ hydrocarbyl, or a substituted or an unsubstituted $C_1$-$C_{12}$ hydrocarbyloxide.

Aspect 51. A continuous process according to any one of the preceding Aspects, wherein the diluent comprises carbon dioxide.

Aspect 52. A continuous process according to any one of the preceding Aspects, wherein at least a portion of the diluent comprises the α,β-unsaturated carboxylic acid or the salt thereof, formed in the process.

Aspect 53. A continuous process according to any one of Aspects 1-50, wherein the diluent comprises any suitable non-protic solvent, or any non-protic solvent disclosed herein.

Aspect 54. A continuous process according to any one of Aspects 1-50, wherein the diluent comprises any suitable non-protic solvent or any non-protic solvent disclosed herein, and carbon dioxide ($CO_2$) under pressure.

Aspect 55. A continuous process according to any one of Aspects 1-50, wherein the diluent comprises any suitable non-protic solvent or any non-protic solvent disclosed herein, and the olefin and carbon dioxide ($CO_2$) under pressure.

Aspect 56. A continuous process according to any one of Aspects 1-50, wherein the diluent comprises carbon dioxide ($CO_2$) under pressure.

Aspect 57. A continuous process according to any one of Aspects 1-50, wherein the diluent comprises the olefin and carbon dioxide ($CO_2$) under pressure.

Aspect 58. A continuous process according to any one of Aspects 1-50, wherein the diluent comprises the ethylene and carbon dioxide ($CO_2$) under pressure.

Aspect 59. A continuous process according to any one of Aspects 1-50, wherein the diluent comprises any suitable weakly coordinating or non-coordinating solvent, or any weakly coordinating or non-coordinating solvent disclosed herein.

Aspect 60. A continuous process according to any one of Aspects 1-50, wherein the diluent comprises any suitable aromatic hydrocarbon solvent, or any aromatic hydrocarbon solvent disclosed herein, e.g., benzene, xylene, toluene, etc.

Aspect 61. A continuous process according to any one of Aspects 1-50, wherein the diluent comprises any suitable ether solvent, or any ether solvent disclosed herein, e.g., THF, dimethyl ether, diethyl ether, dibutyl ether, etc.

Aspect 62. A continuous process according to any one of Aspects 1-50, wherein the diluent comprises any suitable carbonyl-containing solvent, or any carbonyl-containing solvent disclosed herein, e.g., ketones, esters, amides, etc. (e.g., acetone, ethyl acetate, N,N-dimethylformamide, etc.).

Aspect 63. A continuous process according to any one of Aspects 1-50, wherein the diluent comprises any suitable halogenated aromatic hydrocarbon solvent, or any halogenated aromatic hydrocarbon solvent disclosed herein, e.g., chlorobenzene, dichlorobenzene, etc.

Aspect 64. A continuous process according to any one of Aspects 1-50, wherein the diluent comprises THF, 2,5-$Me_2$THF, methanol, acetone, toluene, chlorobenzene, pyridine, or a combination thereof.

Aspect 65. A continuous process according to any one of Aspects 1-64, wherein the contacting step in the third stage further comprises contacting an additive selected from an acid, a base, or a reductant.

Aspect 66. A continuous process according to any one of Aspects 1-2 or 5-64, wherein the contacting step of the first stage further comprises contacting the transition metal precursor compound comprising at least one first ligand with the at least one second ligand.

Aspect 67. A continuous process according to any one of Aspects 1-2 or 5-64, wherein the contacting step of the first stage comprises contacting (a) the transition metal precursor compound with (b) the at least one second ligand to form a pre-contacted mixture, followed by contacting the pre-contacted mixture with (c) the olefin, (d) carbon dioxide ($CO_2$), and (e) the diluent to form the first composition.

Aspect 68. A continuous process according to any one of Aspects 1-2 or 5-64, wherein the contacting step of the first stage comprises contacting the components (a)-(e) in any order.

Aspect 69. A continuous process according to any one of Aspects 1-64 wherein the contacting step of the second stage comprises contacting the polyanionic solid with a second diluent to form a mixture, followed by contacting the mixture with the first composition to form the second composition.

Aspect 70. A continuous process according to any one of Aspects 1-64, wherein the contacting step of the third stage further comprises contacting the second composition with any suitable acid, or any acid disclosed herein, e.g., HCl, acetic acid, etc.

Aspect 71. A continuous process according to any one of Aspects 1-64, wherein the contacting step of the third stage further comprises contacting the second composition with any suitable solvent, or any solvent disclosed herein, e.g., carbonyl-containing solvents such as ketones, esters, amides, etc. (e.g., acetone, ethyl acetate, N,N-dimethylformamide), alcohols, water, etc.

Aspect 72. A continuous process according to any one of the preceding Aspects, wherein the contacting step of the third stage further comprises heating the second composition to any suitable temperature, or a temperature in any range disclosed herein, e.g., from 50 to 1000° C., from 100 to 800° C., from 150 to 600° C., from 250 to 550° C., etc.

Aspect 73. A continuous process according to any one of the preceding Aspects, wherein the molar yield of the α,β-unsaturated carboxylic acid, or the salt thereof, based on the metalalactone (in those preceding Aspects comprising a metalalactone) or based on the transition metal precursor compound (in those preceding Aspects comprising a transition metal precursor compound) is in any range disclosed herein, e.g., at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, or at least 500%, etc.

Aspect 74. A continuous process according to any one of the preceding Aspects, wherein the contacting step in any one or more of the first stage, the second stage, and/or the third stage is conducted at any suitable pressure or at any pressure disclosed herein, e.g., from 5 psig (34 KPa) to 10,000 psig (68,948 KPa), from 45 psig (310 KPa) to 1000 psig (6,895 KPa), etc.

Aspect 75. A continuous process according to any one of the preceding Aspects, wherein the contacting step in any one or more of the first stage, the second stage, and/or the third stage conducted at any suitable temperature or at any temperature disclosed herein, e.g., from 0° C. to 250° C., from 0° C. to 95° C., from 15° C. to 70° C., etc.

Aspect 76. A continuous process according to any one of the preceding Aspects, wherein the contacting step in any one or more of the second stage and/or the third stage is conducted at any suitable weight hourly space velocity (WHSV) or any WHSV disclosed herein, e.g., from 0.05 to 50 $hr^{-1}$, from 1 to 25 $hr^{-1}$, from 1 to 5 $hr^{-1}$, etc., based on the amount of the polyanionic solid.

Aspect 77. A continuous process according to any one of the preceding Aspects, wherein the process further comprises a step of isolating the α,β-unsaturated carboxylic acid, or the salt thereof, e.g., using any suitable separation/purification procedure or any separation/purification procedure disclosed herein, e.g., evaporation, distillation, chromatography, etc.

Aspect 78. A continuous process according to any one of Aspects 1-77, wherein the polyanionic solid of the contacting step (2) comprises a fixed bed.

Aspect 79. A continuous process according to any one of Aspects 1-77, wherein the polyanionic solid of the contacting step (2) is either formed onto beads or is supported on an inorganic or organic carrier material.

Aspect 80. A continuous process according to any one of Aspects 1-79, wherein the α,β-unsaturated carboxylic acid or a salt thereof comprises any suitable α,β-unsaturated carboxylic acid, or any α,β-unsaturated carboxylic acid disclosed herein, or a salt thereof, e.g., acrylic acid, methacrylic acid, 2-ethylacrylic acid, cinnamic acid, sodium acrylate, potassium acrylate, magnesium acrylate, sodium (meth)acrylate, etc.

Aspect 81. A continuous process according to any one of Aspects 1-2 or 5-80, further comprising a step of contacting a transition metal precursor compound comprising at least one first ligand, at least one second ligand, an olefin, and carbon dioxide ($CO_2$) to form the metalalactone compound.

Aspect 82. A continuous process according to any one of Aspects 3-81, wherein the metalalactone compound comprises the at least one second ligand.

Aspect 83. A continuous process according to any one of Aspects 1-2 or 5-81, wherein the olefin comprises any suitable olefin or any olefin disclosed herein, e.g. ethylene, propylene, butene (e.g., 1-butene), pentene, hexene (e.g., 1-hexene), heptane, octene (e.g., 1-octene), styrene, etc.

Aspect 84. A continuous process according to any one of Aspects 1-2 or 5-81, wherein the olefin is ethylene, and the step of contacting a transition metal precursor compound with an olefin and carbon dioxide ($CO_2$) is conducted using any suitable pressure of ethylene, or any pressure of ethylene disclosed herein, e.g., from 10 psig (69 KPa) to 1,000 psig (6895 KPa), from 25 psig (172 KPa) to 500 psig (3,447 KPa), or from 50 psig (345 KPa) to 300 psig (2,068 KPa), etc.

Aspect 85. A continuous process according to any one of Aspects 1-2 or 5-81, wherein the olefin is ethylene, and the step of contacting a transition metal precursor compound with an olefin and carbon dioxide ($CO_2$) is conducted using a constant addition of the olefin and carbon dioxide to provide the second composition.

Aspect 86. A continuous process according to Aspect 85, wherein the ethylene and carbon dioxide ($CO_2$) are constantly added in an ethylene:$CO_2$ molar ratio of from 3:1 to 1:3.

Aspect 87. A continuous process according to any one of Aspects 1-2 or 5-81, wherein the step of contacting a transition metal precursor compound with the olefin and carbon dioxide ($CO_2$) is conducted using any suitable pressure of $CO_2$, or any pressure of $CO_2$ disclosed herein, e.g., from 20 psig (138 KPa) to 2,000 psig (13,790 KPa), from 50 psig (345 KPa) to 750 psig (5,171 KPa), or from 100 psig (689 KPa) to 300 psig (2,068 KPa), etc.

Aspect 88. A continuous process according to any one of the preceding Aspects, further comprising a step of monitoring the concentration of at least one second composition, at least one elimination reaction product, or a combination thereof.

Aspect 89. A continuous process according to any one of Aspects 1-88, wherein the metal of the metalalactone or the metal of the transition metal precursor compound is a Group 6 or 8-11 transition metal.

Aspect 90. A continuous process according to any one of Aspects 1-88, wherein the metal of the metalalactone or the metal of the transition metal precursor compound is Cr, Mo, W, Fe, Co, Ni, Cu, Ru, Rh, Pd, Ag, Ir, Pt, or Au.

Aspect 91. A continuous process according to any one of Aspects 1-88, wherein the metal of the metalalactone or the metal of the transition metal precursor compound is Ni, Fe, or Rh.

Aspect 92. A continuous process according to any one of Aspects 1-88, wherein the metal of the metalalactone or the metal of the transition metal precursor compound is Ni.

Aspect 93. A continuous process according to any one of Aspects 1-88, wherein the metalalactone is a nickelalactone, e.g., any suitable nickelalactone or any nickelalactone disclosed herein.

Aspect 94. A continuous process according to any one of Aspects 1-93, wherein any of the first ligand, or the second ligand is any suitable neutral electron donor group and/or Lewis base, or any neutral electron donor group and/or Lewis base disclosed herein.

Aspect 95. A continuous process according to any one of Aspects 1-93, wherein any of the first ligand, or the second ligand is a bidentate ligand.

Aspect 96. A continuous process according to any one of Aspects 1-93, wherein any of the first ligand, or the second ligand comprises an olefin ligand or a diene ligand.

Aspect 97. A continuous process according to any one of Aspects 1-93, wherein any of the first ligand, or the second ligand comprises at least one of a nitrogen, phosphorus, sulfur, or oxygen heteroatom.

Aspect 98. A continuous process according to any one of Aspects 1-93, wherein any of the first ligand, or the second ligand comprises or is selected from a diphosphine ligand, a diamine ligand, a diene ligand, a diether ligand, or dithioether ligand.

Aspect 99. A continuous process according to any one of Aspects 1-93, wherein the first ligand is a diene ligand and the second ligand is a diphosphine ligand.

Aspect 100. A continuous process according to any one of Aspects 1-99, further comprising a step of washing the regenerated polyanionic solid with a solvent or the diluent following the third stage.

Aspect 101. A continuous process according to any one of Aspects 1-100, wherein the metal-containing base comprises any suitable base, or any base disclosed herein, e.g., carbonates (e.g., $Na_2CO_3$, $Cs_2CO_3$, $MgCO_3$), hydroxides (e.g., $Mg(OH)_2$, NaOH), alkoxides (e.g., $Al(O^iPr)_3$, $Na(O^tBu)$, $Mg(OEt)_2$), halides (e.g. NaCl, KCl, LiI) and the like.

Aspect 102. A continuous process according to any one of Aspects 1-101, wherein the step of contacting the reacted solid with the metal-containing base is carried out in the absence of an alkoxide, an aryloxide, an amide, an alkylamide, an arylamide, an amine, a hydride, a phosphazene, and/or substituted analogs thereof.

Aspect 103. A continuous process according to any one of Aspects 1-101, wherein the step of contacting the reacted solid with the metal-containing base is carried out in the absence of an alkoxide, an aryloxide, a hydride, and/or a phosphazene.

Aspect 104. A continuous process according to any one of Aspects 1-101, wherein the step of contacting the reacted solid with the metal-containing base is carried out in the absence of an aryloxide or a metal hydride.

Aspect 105. A continuous process according to any one of Aspects 1-101, wherein the step of contacting the reacted solid with the metal-containing base is carried out in the absence of a non-nucleophilic base.

Aspect 106. A continuous process according to any one of Aspects 1-105, wherein the polyanionic solid is unsupported.

Aspect 107. A continuous process according to any one of Aspects 1-105, wherein the polyanionic solid is supported.

Aspect 108. A continuous process according to any one of the preceding Aspects, wherein the metalalactone compound, any ligand of the metalalactone compound, transition metal precursor compound, first ligand, second ligand, polyanionic solid, or metal cation is any suitable metalalactone compound, ligand of the metalalactone compound, transition metal precursor compound, first ligand, second ligand, polyanionic solid, or metal cation or is any metalalactone compound, ligand of the metalalactone compound, transition metal precursor compound, first ligand, second ligand, polyanionic solid, or metal cation disclosed herein.

Aspect 109. A continuous process for producing an $\alpha,\beta$-unsaturated carboxylic acid or salt thereof, the process comprising:
1) in a first stage, contacting (a) a Group 8-10 transition metal precursor compound comprising at least one first ligand, (b) optionally, at least one second ligand, (c) an olefin, (d) carbon dioxide ($CO_2$), and (e) a diluent to form a first composition comprising a metalalactone compound; and
2) in a second stage, contacting an anionic polyaromatic resin comprising associated metal cations with the first composition to form a second composition comprising an adduct of the metalalactone compound and the anionic polyaromatic resin; and
3) in a third stage, (a) contacting the second composition with water to release a metal salt of an $\alpha,\beta$-unsaturated carboxylic acid and form a reacted polyaromatic resin; and (b) contacting the reacted polyaromatic resin with a metal-containing base to produce a regenerated polyanionic solid.

Aspect 110. A continuous process according to Aspect 109, wherein the anionic polyaromatic resin comprises an alkali metal or an alkaline earth metal oxide, hydroxide, alkoxide, aryloxide, amide, alkyl amide, arylamide, or carbonate.

Aspect 111. A continuous process according to any one of Aspects 109-110, wherein the contacting step is carried out in the absence of a non-nucleophilic base.

We claim:
1. A continuous process for producing an $\alpha,\beta$-unsaturated carboxylic acid or salt thereof, the process comprising
   1) in a first stage, contacting (a) a Group 6 or a Group 8-11 transition metal precursor compound comprising at least one first ligand, (b) optionally, at least one second ligand, (c) an olefin, (d) carbon dioxide ($CO_2$), and (e) a diluent to form a first composition; and
   2) in a second stage, contacting a polyanionic solid with associated cations with the first composition to form a second composition; and
   3) in a third stage, (a) contacting the second composition with a polar solvent to release a metal salt of an $\alpha,\beta$-unsaturated carboxylic acid and form a reacted solid; and (b) contacting the reacted solid with a metal-containing base to produce a regenerated polyanionic solid with associated cations.

2. A continuous process according to claim 1, wherein the polar solvent comprises water, an aliphatic alcohol, an aromatic alcohol, an inorganic acid, an organic acid, or a combination thereof.

3. A continuous process according to claim 1, wherein the first stage and the second stage are carried out: a) concurrently in a first reactor and a second reactor, respectively; or b) sequentially in a single reactor.

4. A continuous process according to claim 1, further comprising, in a fourth stage, drying or partially drying the regenerated polyanionic solid with associated cations.

5. A continuous process according to claim 4, wherein the second stage, the third stage, and the fourth stage are carried out: a) concurrently in a second reactor, a third reactor, and a fourth reactor, respectively; or b) sequentially in a single reactor.

6. A continuous process according to claim 1, wherein the polyanionic solid with associated cations comprises a poly(vinyl aryloxide), a poly(vinyl alkoxide), a poly(acrylate), a poly((meth)acrylate), a poly(styrene sulfonate), a phenol-formaldehyde resin, a polyhydroxyarene-formaldehyde resin, a polyhydroxyarene- and fluorophenol-formaldehyde resin, a poly(vinyl arylamide), a poly(vinyl alkylamide), or combinations thereof.

7. A continuous process according to claim 1, wherein the polyanionic solid with associated cations comprises associated metal cations selected from lithium, sodium, potassium, magnesium, calcium, strontium, barium, aluminum, or zinc.

8. A continuous process according to claim 1, wherein the polyanionic solid with associated cations comprises a chemically-treated solid oxide comprising at least one solid oxide that has been treated with at least one electron withdrawing anion.

9. A continuous process according to claim 8, wherein the chemically-treated solid oxide further comprises water.

10. A continuous process according to claim 8, wherein the at least one solid oxide comprises at least one of silica, alumina, silica-alumina, silica-coated alumina, aluminum phosphate, aluminophosphate, heteropolytungstate, mullite, titania, zirconia, magnesia, boria, zinc oxide, silica-titania, silica-zirconia, a mixed oxide thereof, or any mixture thereof, that has been chemically treated with at least one electron withdrawing anion; and
wherein the at least one electron withdrawing anion comprises fluoride, chloride, bromide, iodide, phosphate, triflate, trifluoroacetate, sulfate, bisulfate, fluorosulfate, fluoroborate, fluorophosphate, fluorozirconate, fluorotitanate, phosphotungstate, or any combination thereof.

11. A continuous process according to claim 1, wherein the polyanionic solid with associated cations comprises an organic base moiety immobilized on a solid support comprises structural units having the general formula (I):

wherein SS is a solid support, A is an anchor moiety, L is a direct bond or linking moiety, and B is an organic base moiety, and x is 0 to 3; and
wherein the organic base moiety B has the general formula:

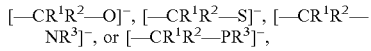

wherein each of $R^1$ and $R^2$, independently or together, are selected from H or an unbranched or branched, acyclic or cyclic, $C_1$-$C_{12}$ hydrocarbyl residue; and $R^3$ is selected independently from hydrogen or a substituted or an unsubstituted $C_1$-$C_{12}$ hydrocarbyl.

12. A continuous process according to claim 1, wherein the diluent comprises a non-protic solvent, carbon dioxide ($CO_2$), and/or at the α,β-unsaturated carboxylic acid or the salt thereof, formed in the process.

13. A continuous process according to claim 1, wherein the metal of the transition metal precursor compound is Cr, Mo, W, Fe, Co, Ni, Cu, Ru, Rh, Pd, Ag, Ir, Pt, or Au, and wherein any of the first ligand, or the second ligand comprises at least one of a nitrogen, phosphorus, sulfur, or oxygen heteroatom.

14. A continuous process for producing an α,β-unsaturated carboxylic acid or salt thereof, the process comprising
1) in a first stage, contacting (a) a Group 6 or a Group 8-11 transition metal precursor compound comprising at least one first ligand, (b) optionally, at least one second ligand, (c) an olefin, (d) carbon dioxide ($CO_2$), and (e) a diluent to form a first composition comprising a metalalactone compound; and
2) in a second stage, contacting a polyanionic solid with associated cations with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid with associated cations.

15. A continuous process according to claim 14, wherein the second composition comprises an adduct of the metalalactone compound and the polyanionic solid with associated cations.

16. A continuous process according to claim 14, wherein the metal of the metalalactone compound is Cr, Mo, W, Fe, Co, Ni, Cu, Ru, Rh, Pd, Ag, Ir, Pt, or Au, and wherein any of the first ligand, or the second ligand comprises at least one of a nitrogen, phosphorus, sulfur, or oxygen heteroatom.

17. A continuous process according to claim 14, wherein the polyanionic solid with associated cations comprises a poly(vinyl aryloxide), a poly(vinyl alkoxide), a poly(acrylate), a poly((meth)acrylate), a poly(styrene sulfonate), a phenol-formaldehyde resin, a polyhydroxyarene-formaldehyde resin, a polyhydroxyarene- and fluorophenol-formaldehyde resin, a poly(vinyl arylamide), a poly(vinyl alkylamide), or combinations thereof.

18. A continuous process according to claim 14, wherein the polyanionic solid with associated cations comprises associated metal cations selected from lithium, sodium, potassium, magnesium, calcium, strontium, barium, aluminum, or zinc.

19. A continuous process according to claim 14, wherein the polyanionic solid with associated cations comprises a chemically-treated solid oxide comprising at least one solid oxide that has been treated with at least one electron withdrawing anion.

20. A continuous process according to claim 19, wherein the chemically-treated solid oxide further comprises water.

21. A continuous process according to claim 19, wherein:
the at least one solid oxide comprises at least one of silica, alumina, silica-alumina, silica-coated alumina, aluminum phosphate, aluminophosphate, heteropolytungstate, mullite, titania, zirconia, magnesia, boria, zinc oxide, silica-titania, silica-zirconia, a mixed oxide thereof, or any mixture thereof, that has been chemically treated with at least one electron withdrawing anion; and
wherein the at least one electron withdrawing anion comprises fluoride, chloride, bromide, iodide, phosphate, triflate, trifluoroacetate, sulfate, bisulfate, fluorosulfate, fluoroborate, fluorophosphate, fluorozirconate, fluorotitanate, phosphotungstate, or any combination thereof.

22. A continuous process for producing an α,β-unsaturated carboxylic acid or salt thereof, the process comprising
1) in a first stage, obtaining or providing a first composition comprising a metalalactone compound of a Group 6 or a Group 8-11 transition metal and a diluent;
2) in a second stage, contacting a polyanionic solid with associated cations with the first composition to form a second composition; and
3) in a third stage, (a) contacting the second composition with a polar solvent to release a metal salt of an α,β-unsaturated carboxylic acid and form a reacted solid; and (b) contacting the reacted solid with a metal-containing base to produce a regenerated polyanionic solid with associated cations.

23. A continuous process according to claim 22, wherein the second composition comprising an adduct of the metalalactone compound and the polyanionic solid with associated cations.

24. A continuous process according to claim 6, wherein the polyanionic solid with associated cations comprises a resorcinol-formaldehyde resin, a resorcinol- and 2-fluorophenol-formaldehyde resin, or combinations thereof.

25. A continuous process according to claim 17, wherein the polyanionic solid with associated cations comprises a resorcinol-formaldehyde resin, a resorcinol- and 2-fluorophenol-formaldehyde resin, or combinations thereof.

* * * * *

UNITED STATES PATENT AND TRADEMARK OFFICE
CERTIFICATE OF CORRECTION

PATENT NO. : 10,544,080 B2
APPLICATION NO. : 16/001171
DATED : January 28, 2020
INVENTOR(S) : M. L. Hlavinka et al.

It is certified that error appears in the above-identified patent and that said Letters Patent is hereby corrected as shown below:

In the Specification

Column 2, Line 1, please change "an" to --a--
Column 5, Line 44, please insert --describe-- between "to" and "a"
Column 10, Line 44, please change "an" to --a--
Column 12, Lines 56-57, please insert --or-- between "anion," and "treated"
Column 12, Line 57, please change "oxide," and --oxide.--
Column 14, Line 59, please change "described" to --describe--
Column 16, Line 26, please change "fluoro sulfate" to --fluorosulfate--
Column 16, Lines 30-31, please change "fluoro sulfate" to --fluorosulfate--
Column 17, Line 2, please change "an" to --a--
Column 25, Line 27, please insert --be-- between "can" and "Au"
Column 29, Line 58, please change "comprises" to --comprise--
Column 30, Line 40, please change "figures" to --figure--
Column 32, Line 65, please change "long of" to --long as--
Column 40, Line 45, please change "describe" to --describes--
Column 42, Line 31, please change "involve" to --involves--

Signed and Sealed this
Nineteenth Day of May, 2020

Andrei Iancu
*Director of the United States Patent and Trademark Office*